(12) United States Patent
Fassih et al.

(10) Patent No.: US 8,744,567 B2
(45) Date of Patent: Jun. 3, 2014

(54) GALVANIC SKIN TREATMENT DEVICE

(75) Inventors: Ali Fassih, Franklin Park, NJ (US);
Ronald J. Gillespie, North Brunswick, NJ (US); Jue-Chen Liu, Belle Mead, NJ (US); Chong Jin Loy, Singapore (SG); Claude Saliou, Basking Ridge, NJ (US); Ying Sun, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 572 days.

(21) Appl. No.: 12/941,117

(22) Filed: Nov. 8, 2010

(65) Prior Publication Data

US 2011/0118655 A1    May 19, 2011

Related U.S. Application Data

(60) Provisional application No. 61/261,084, filed on Nov. 13, 2009.

(51) Int. Cl.
*A61N 1/30* (2006.01)

(52) U.S. Cl.
USPC ............................................................ 604/20

(58) Field of Classification Search
CPC . A61K 9/0014; A61K 2800/83; A61K 33/00; A61N 1/205; A61N 1/325; A61N 1/044; A61N 1/0448; A61N 1/0436; A61N 1/30; A61N 1/0428; A61N 1/0456; A61N 1/0468; A61N 1/0484; A61N 1/0492; A61N 1/042; A61N 1/0424; A61N 1/0432; A61N 1/0452; A61N 1/0464; A61N 1/20

USPC ...................................... 604/20–22; 607/116
See application file for complete search history.

(56) References Cited

U.S. PATENT DOCUMENTS

| | | | |
|---|---|---|---|
| 4,067,342 A | 1/1978 | Burton |
| 4,211,222 A | 7/1980 | Tapper |
| 4,305,390 A | 12/1981 | Swartz |
| 4,372,296 A | 2/1983 | Fahim |
| 4,406,658 A | 9/1983 | Lattin et al. |
| 4,474,570 A | 10/1984 | Ariura et al. |
| 4,606,354 A | 8/1986 | Jacob |
| 4,689,039 A | 8/1987 | Masaki |
| 4,764,164 A | 8/1988 | Sasaki |
| 4,767,401 A | 8/1988 | Seiderman |
| 4,842,577 A | 6/1989 | Konno et al. |

(Continued)

FOREIGN PATENT DOCUMENTS

| | | |
|---|---|---|
| DE | 19831798 A1 | 1/2000 |
| EP | 0 337 642 A | 10/1989 |

(Continued)

OTHER PUBLICATIONS

Int'l. Search Report for Application No. PCT/US2010/055819, dated Feb. 17, 2011.

(Continued)

*Primary Examiner* — Manuel Mendez
(74) *Attorney, Agent, or Firm* — Sharon E. Hayner

(57) ABSTRACT

A galvanic device for treatment of skin is provided. The device comprises a substrate comprising a plurality of discrete galvanic couples, each galvanic couple comprising a first conductive electrode that is an anode in electronic communication with a second conductive electrode that is a cathode.

28 Claims, 9 Drawing Sheets

(56) References Cited

U.S. PATENT DOCUMENTS

| | | | |
|---|---|---|---|
| 4,852,571 A | 8/1989 | Gadsby et al. |
| 4,956,184 A | 9/1990 | Kross |
| 4,957,480 A | 9/1990 | Morenings |
| 4,979,938 A | 12/1990 | Stephen et al. |
| 5,042,975 A | 8/1991 | Cien et al. |
| 5,084,006 A | 1/1992 | Lew et al. |
| 5,122,418 A | 6/1992 | Nakane et al. |
| 5,147,297 A | 9/1992 | Myers et al. |
| 5,162,043 A | 11/1992 | Lew et al. |
| 5,224,927 A | 7/1993 | Tapper |
| 5,298,017 A | 3/1994 | Theeuwes et al. |
| 5,314,502 A | 5/1994 | McNichols et al. |
| 5,326,341 A | 7/1994 | Lew et al. |
| 5,338,412 A | 8/1994 | Burk et al. |
| 5,352,315 A | 10/1994 | Carrier et al. |
| 5,356,632 A | 10/1994 | Gross et al. |
| 5,380,272 A | 1/1995 | Gross |
| 5,384,134 A | 1/1995 | Kross et al. |
| 5,387,189 A | 2/1995 | Gory et al. |
| 5,405,317 A | 4/1995 | Myers et al. |
| 5,415,628 A | 5/1995 | Untereker et al. |
| 5,428,185 A | 6/1995 | Kunimoto et al. |
| 5,443,441 A * | 8/1995 | De Claviere ............... 604/20 |
| 5,466,217 A | 11/1995 | Myers et al. |
| 5,470,349 A | 11/1995 | Kleditsch et al. |
| 5,503,840 A | 4/1996 | Jacobson et al. |
| 5,624,415 A | 4/1997 | Ledger et al. |
| 5,624,425 A | 4/1997 | Gray et al. |
| 5,637,084 A | 6/1997 | Kontturi et al. |
| 5,678,545 A * | 10/1997 | Stratbucker ............... 600/393 |
| 5,685,837 A | 11/1997 | Horstmann |
| 5,688,233 A | 11/1997 | Hofmann et al. |
| 5,817,044 A | 10/1998 | Evers et al. |
| 5,830,175 A | 11/1998 | Flower |
| 5,855,570 A | 1/1999 | Scherson et al. |
| 5,897,522 A | 4/1999 | Nitzan |
| 5,928,185 A | 7/1999 | Muller et al. |
| 5,935,598 A | 8/1999 | Sage et al. |
| 5,955,017 A | 9/1999 | Fofano et al. |
| 5,955,067 A | 9/1999 | Oge et al. |
| 5,961,483 A | 10/1999 | Sage et al. |
| 5,974,344 A | 10/1999 | Shoemaker, II |
| 5,985,308 A | 11/1999 | Burrell et al. |
| 5,993,435 A | 11/1999 | Haak et al. |
| 6,004,309 A | 12/1999 | Phipps |
| 6,038,485 A | 3/2000 | Axelgaard |
| 6,078,842 A | 6/2000 | Gross et al. |
| 6,104,950 A | 8/2000 | Higo et al. |
| 6,113,636 A | 9/2000 | Ogle |
| 6,157,858 A | 12/2000 | Gross et al. |
| 6,169,920 B1 | 1/2001 | Haak et al. |
| 6,185,453 B1 | 2/2001 | Hussain et al. |
| 6,223,076 B1 | 4/2001 | Tapper |
| 6,231,830 B1 | 5/2001 | Madray |
| 6,238,381 B1 | 5/2001 | Tapper |
| 6,248,449 B1 | 6/2001 | Watanabe |
| RE37,263 E | 7/2001 | Kross et al. |
| 6,275,372 B1 | 8/2001 | Vassallo et al. |
| 6,289,241 B1 | 9/2001 | Phipps |
| 6,302,874 B1 | 10/2001 | Zhang et al. |
| 6,306,384 B1 | 10/2001 | Lahanas et al. |
| 6,317,629 B1 | 11/2001 | Haak et al. |
| 6,385,487 B1 | 5/2002 | Henley |
| 6,421,561 B1 | 7/2002 | Morris |
| 6,424,862 B1 | 7/2002 | Brown, III et al. |
| 6,443,978 B1 | 9/2002 | Zharov |
| 6,455,065 B1 | 9/2002 | Hymes |
| 6,488,965 B1 | 12/2002 | Karageozian |
| 6,494,900 B1 | 12/2002 | Salansky et al. |
| 6,495,158 B1 | 12/2002 | Buseman et al. |
| 6,522,918 B1 | 2/2003 | Crisp et al. |
| 6,544,401 B1 | 4/2003 | Colic |
| 6,552,895 B1 | 4/2003 | Vassallo et al. |
| 6,560,483 B1 | 5/2003 | Kumar et al. |
| 6,582,416 B2 | 6/2003 | Tapper |
| 6,584,349 B1 | 6/2003 | Sage, Jr. et al. |
| 6,631,294 B2 | 10/2003 | Andino et al. |
| 6,653,014 B2 | 11/2003 | Anderson et al. |
| 6,654,635 B1 | 11/2003 | Koga et al. |
| 6,708,050 B2 | 3/2004 | Carim |
| 6,735,470 B2 | 5/2004 | Henley et al. |
| 6,738,662 B2 | 5/2004 | Frank |
| 6,745,071 B1 | 6/2004 | Anderson et al. |
| 6,766,202 B2 | 7/2004 | Underwood et al. |
| 6,775,570 B2 | 8/2004 | Joshi |
| 6,821,281 B2 | 11/2004 | Sherman et al. |
| 6,855,117 B2 | 2/2005 | Skover |
| 6,866,856 B2 | 3/2005 | Lu et al. |
| 6,890,553 B1 | 5/2005 | Sun et al. |
| 6,989,156 B2 | 1/2006 | Gillis |
| 7,005,408 B2 | 2/2006 | Ahmad et al. |
| 7,008,647 B2 | 3/2006 | Burrell et al. |
| 7,457,667 B2 | 11/2008 | Skiba |
| 7,476,221 B2 | 1/2009 | Sun et al. |
| 7,476,222 B2 | 1/2009 | Sun et al. |
| 7,477,938 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,480,530 B2 | 1/2009 | Sun et al. |
| 7,486,989 B2 | 2/2009 | Sun et al. |
| 7,495,146 B2 | 2/2009 | Crisp |
| 7,507,228 B2 | 3/2009 | Sun et al. |
| 8,025,673 B1 * | 9/2011 | Lyapko ............... 606/189 |
| 8,150,525 B2 | 4/2012 | Sun et al. |
| 8,239,017 B2 | 8/2012 | Sun et al. |
| 2002/0099320 A1 * | 7/2002 | Beck ............... 604/20 |
| 2002/0173743 A1 | 11/2002 | Tapper |
| 2002/0173833 A1 | 11/2002 | Korman et al. |
| 2002/0182485 A1 | 12/2002 | Anderson et al. |
| 2002/0183685 A1 | 12/2002 | Crawford et al. |
| 2002/0188241 A1 | 12/2002 | Morris et al. |
| 2003/0023270 A1 | 1/2003 | Danz et al. |
| 2003/0028170 A1 | 2/2003 | Anderson et al. |
| 2003/0039860 A1 | 2/2003 | Cheon et al. |
| 2003/0054046 A1 | 3/2003 | Burrell |
| 2003/0059673 A1 | 3/2003 | Langan et al. |
| 2003/0100884 A1 | 5/2003 | Deagle |
| 2003/0149393 A1 | 8/2003 | Joshi |
| 2003/0176832 A1 | 9/2003 | Rossi |
| 2003/0216783 A1 * | 11/2003 | Lehtoluoto ............... 607/2 |
| 2004/0006374 A1 | 1/2004 | Mondin |
| 2004/0043062 A1 | 3/2004 | Sun et al. |
| 2004/0044384 A1 | 3/2004 | Leber et al. |
| 2004/0167460 A1 | 8/2004 | Anderson et al. |
| 2004/0167461 A1 | 8/2004 | Nitzan |
| 2004/0265395 A1 | 12/2004 | Sun et al. |
| 2004/0267189 A1 | 12/2004 | Mavor |
| 2004/0267190 A1 | 12/2004 | Tamarkin et al. |
| 2004/0267236 A1 | 12/2004 | Sun et al. |
| 2004/0267237 A1 | 12/2004 | Sun et al. |
| 2005/0004508 A1 * | 1/2005 | Sun et al. ............... 604/20 |
| 2005/0004509 A1 | 1/2005 | Sun et al. |
| 2005/0010192 A1 | 1/2005 | Sun et al. |
| 2005/0148996 A1 | 7/2005 | Sun et al. |
| 2006/0015052 A1 | 1/2006 | Crisp |
| 2006/0015053 A1 | 1/2006 | Crisp |
| 2006/0133134 A1 | 6/2006 | Doyle et al. |
| 2007/0003516 A1 | 1/2007 | Almond et al. |
| 2007/0060862 A1 | 3/2007 | Sun et al. |
| 2007/0122461 A1 | 5/2007 | Ko |
| 2007/0141173 A1 | 6/2007 | Miyamoto et al. |
| 2007/0191756 A1 | 8/2007 | Tapper |
| 2008/0050452 A1 | 2/2008 | Chen et al. |
| 2008/0312579 A1 | 12/2008 | Chang et al. |
| 2009/0076479 A1 | 3/2009 | Sun et al. |
| 2009/0123733 A1 | 5/2009 | Ohrlander et al. |
| 2009/0292328 A1 | 11/2009 | Birkill et al. |
| 2010/0057147 A1 | 3/2010 | Fassih et al. |
| 2011/0118655 A1 | 5/2011 | Fassih et al. |

(56) References Cited

U.S. PATENT DOCUMENTS

FOREIGN PATENT DOCUMENTS

| | | | |
|---|---|---|---|
| EP | 0 532 451 A | 3/1993 |
| EP | 1008 365 A | 6/2000 |
| EP | 1 484 012 A | 12/2004 |
| GB | 2206493 A | 1/1989 |
| JP | 03080874 A | 4/1991 |
| JP | 10024108 A | 1/1998 |
| RU | 45627 | 5/2005 |
| WO | WO 89/01764 A1 | 3/1989 |
| WO | WO 93/00959 A | 1/1993 |
| WO | WO 93/14813 A1 | 8/1993 |
| WO | WO 94/11058 A | 5/1994 |
| WO | WO 94/16765 A1 | 8/1994 |
| WO | WO 94/17853 A1 | 8/1994 |
| WO | WO 95/23588 A1 | 9/1995 |
| WO | WO 97/06847 A | 2/1997 |
| WO | WO 98/14237 A | 4/1998 |
| WO | WO 99/43382 A | 2/1999 |
| WO | WO 99/56819 A | 11/1999 |
| WO | WO 00/12173 A | 3/2000 |
| WO | WO 00/37071 A1 | 8/2000 |
| WO | WO 00/47274 A1 | 8/2000 |
| WO | WO 00/62856 A1 | 10/2000 |
| WO | WO 00/62857 A1 | 10/2000 |
| WO | WO 00/74772 A | 12/2000 |
| WO | WO 01/80945 A | 11/2001 |
| WO | WO 02/092167 A1 | 11/2002 |
| WO | WO 02/098502 A | 12/2002 |
| WO | WO 03/066156 A2 | 8/2003 |
| WO | WO 03/082095 A | 10/2003 |
| WO | WO 2005/004979 A1 | 1/2005 |
| WO | WO 2005/004981 A2 | 1/2005 |
| WO | WO 2005/004982 A2 | 1/2005 |
| WO | WO 2005/004983 A2 | 1/2005 |
| WO | WO 2005/004984 A | 1/2005 |
| WO | WO 2005/079913 A1 | 9/2005 |
| WO | WO 2006/133134 A2 | 12/2006 |
| WO | WO 2008/079898 A1 | 7/2008 |
| WO | WO 2009/045720 A2 | 4/2009 |

OTHER PUBLICATIONS

Int'l. Search Report for Application No. PCT/US2009/054903, dated Nov. 17, 2009.
Janotti, A. et al., "Fundamentals of Zinc Oxide as a Semiconductor", Reports on Progress in Physics, 72 (2009), 126510, pp. 1-29.
Data Sheet: Patch Publicity Available prior to Jun. 30, 2003.
Electrochemistry Handbook, Table 14.1: ;McGraw Hill Inc. (1995) pp. 14-3-14.16.
Davis, "Can Acupuncture Punch Up Your Appearance?", Wall Street Journal, Health Article Dec. 21, 2004 p. 107.
Li, etal. Ultra Zinc and Nickel, Palladium, Silvercoated Zinc Particles Used for Reductive Dehalogenation of Chlorinated Ethylenes in Aqueoussolution, Croatica Chemical ACTA CCACAA 71 (1998) vol. 4,pp. 853-872.
Ly Chan et al., Treatment of palmar hyperhidrosis using tap water iontophoresis: local experience: HKMJ, vol. 5, No. 2, Jun. 2, 1999.
Procellera™ bioelectric wound dressing, Vomaris Wound Care, Inc., distributed Oct. 22-25, 2009 at 2009 Clinical Symposium on Advances in Skin and Wound Care, San Antonio, TX.
Sato, et al. "Eneration and Transit Pathway of H+ is Critical for Inhibition of Palmar Sweating by Inotophoresisin Water", J. Applied Physiology, Nov. 1993, vol. 75, pp. 2258-1164.
Spacciapoli, et al. "Antimicrobial Activity of Silver Nitrate Against Peridontal Pathogens" Journal of Peridontal Research (2001) vol. 36,pp. 108-113.
Stux, et al. "Basics of Acupuncture", Springer (2003) pp. 306-309.

* cited by examiner

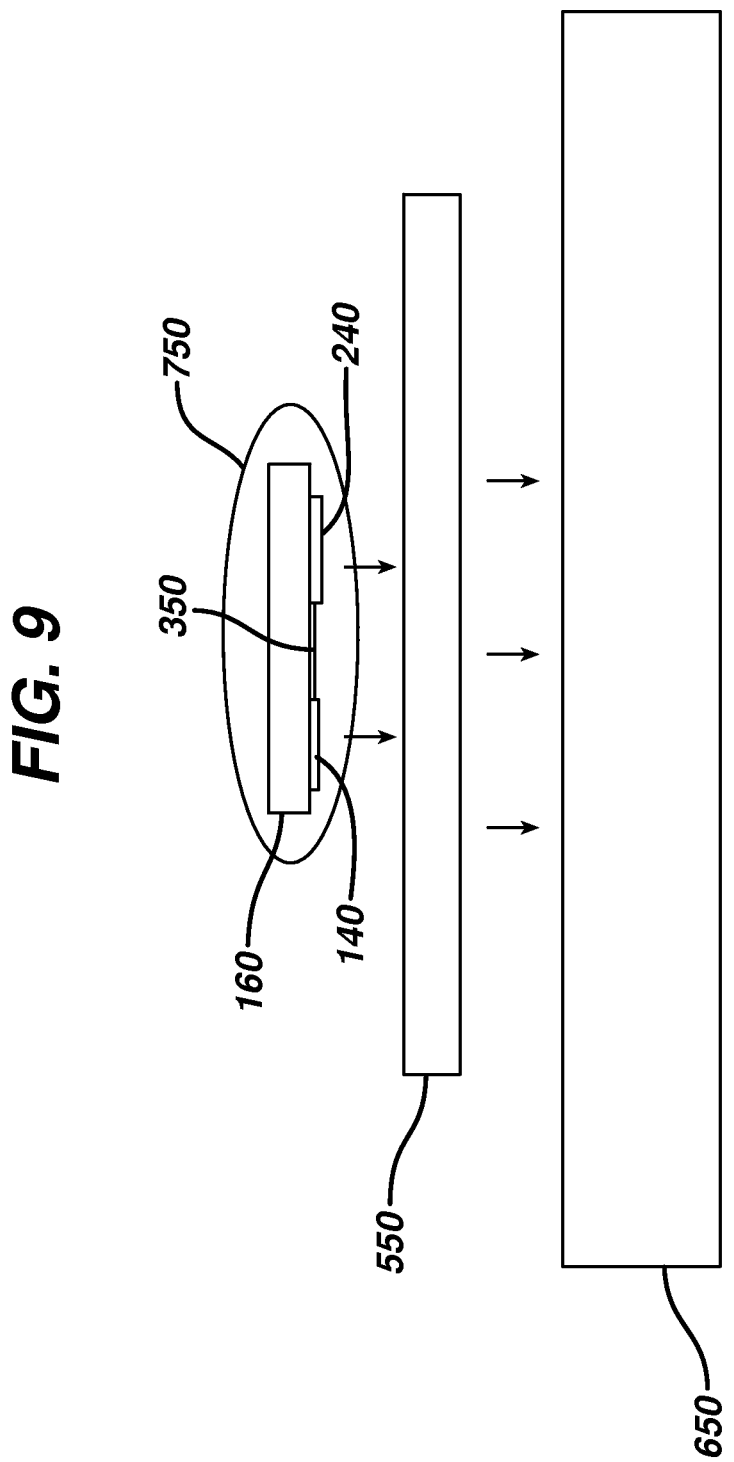

GALVANIC SKIN TREATMENT DEVICE

CROSS REFERENCE TO RELATED APPLICATIONS

This application claims priority of the benefits of the filing of U.S. Provisional Application Ser. No. 61/261,084, filed Nov. 13, 2009. The complete disclosure of the aforementioned related patent application is hereby incorporated herein by reference for all purposes.

BACKGROUND OF THE INVENTION

Use of a galvanic couple as the power source in iontophoresis devices is well known in the art. See, e.g., U.S. Pat. Nos. 5,147,297, 5,162,043, 5,298,017, 5,326,341, 5,405,317, 5,685,837, 6,584,349, 6,421,561 and 6,653,014. Typical materials from which a galvanic couple is made include a silver/zinc donor electrode and a silver/silver chloride counter electrode. Such a combination produces an electric potential of about one volt and activates automatically when body tissue and/or fluids form a complete circuit with the system to generate the electricity.

U.S. Patent Application Publication No. US2007/0060862 discloses galvanic couple-containing devices for treating various tissues and conditions. In one embodiment, such devices may comprise two dissimilar conductive electrodes in a carrier layer connected to each other either through a connective wire or by direct physical contact to form a plurality of galvanic couple power sources. As shown in FIGS. 8-11, the conductive electrodes are in the form continuous structures (such as zinc wire) spanning the carrier layer that touch each other or a connecting wire at several locations.

U.S. Pat. No. 7,457,667 and US Patent Application Publication Nos. US2006/0015052 and US2006/0015053 disclose wound dressings that are said to employ galvanic currents. The wound dressings comprise substrate materials holding areas or particles of two dissimilar metals, such areas or particles in proximity but not touching each other.

Applicants have now discovered improved galvanic skin treatment devices comprising a plurality of discrete galvanic couples that comprise conductive electrodes in electronic communication with one another on a substrate. Such galvanic couples are detached from each other, generally of a small size, and of variable shape and positioning on the substrate. In one embodiment, the substrate is made of paper.

Advantageously, use of a plurality of galvanic couples on the substrate, i.e., a galvanic couple array, enables the tailored and controlled distribution of multiple positive and negative poles over a treatment area and consequently a very uniform electricity distribution to the tissue under treatment. This is not possible with conventional electrical devices that offer only one anode and one cathode, or devices that contain scattered metallic particles. Because each galvanic couple acts independently of surrounding ones, each galvanic couple exclusively treats the skin directly adjacent to it. Therefore, a plurality of galvanic couples provides a uniformly distributed dose of electricity to the treatment area. Another advantage of this effect is that the maximum dose of electricity is controlled by the output of each galvanic couple. This is particularly advantageous if a portion of the treatment area has varying conductivity or compromised skin integrity, such as with a wound (e.g. the maximum current supplied is limited to that provided by the local galvanic couples only). The present device also enables flexibility for a user in terms of shape and size. For example, a nurse can produce a desirably sized and shaped wound dressing to fit a chronic wound/lesion (which might be of any shape or size) from a device of the invention without disabling the galvanic couples.

SUMMARY OF THE INVENTION

The present invention provides a device for treatment of skin comprising a substrate comprising a plurality of discrete galvanic couples, each galvanic couple comprising a first conductive electrode that is an anode in electronic communication with a second conductive electrode that is a cathode.

The invention also provides a method of treating skin comprising applying the above device to said skin.

The invention also provides a skin treatment product comprising a facial mask and the above device, wherein the device is of a shape and size suitable for overlaying or underlying the facial mask during use, i.e., while the facial mask and device are applied to the skin.

Other features and advantages of the present invention will be apparent from the detailed description of the invention and from the claims.

BRIEF DESCRIPTION OF THE DRAWINGS

FIG. 9 is a top view of a skin treatment product according to the invention comprising a device 750 overlaying a facial mask 550 which is placed against the skin 650.

DETAILED DESCRIPTION OF THE INVENTION

Figure 1:
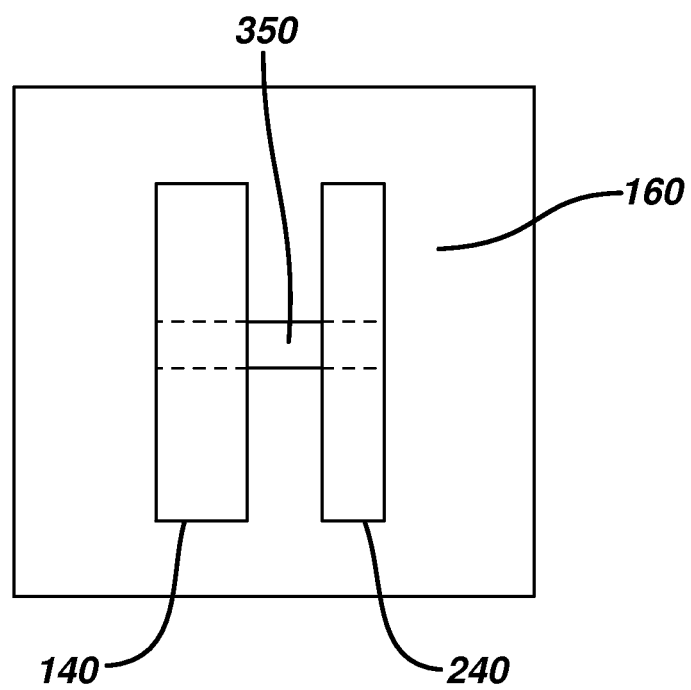
FIG. 1 is a top view of a single galvanic couple according to the invention in which conductive electrodes 140 and 240 are brought into electrical communication by a connecting bridge comprising a conductive material 350.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)).

Although the invention is described herein with respect to the treatment of skin, the devices, methods and products of the invention are applicable to any human or animal barrier membrane including the skin or eye (cornea, retina, etc.), oral, buccal, nasal, vaginal, gastrointestinal, or rectal mucosa, or wounds, lesions, or nails.

What is meant by a "product" is a product in finished packaged form. In one embodiment, the product contains instructions directing the user to apply the device to a barrier membrane (e.g., to treat a skin condition). Such instructions may be printed on the product, label insert, or on any additional packaging.

In one aspect, the present invention features promoting a device or product of the present invention for its intended use. What is meant by "promoting" is promoting, advertising, or marketing. Examples of promoting include, but are not limited to, written, visual, or verbal statements made on the product or in stores, magazines, newspaper, radio, television, internet, and the like.

As used herein, "pharmaceutically-acceptable" means suitable for use in contact with a barrier membrane (e.g., the skin or mucosa) without undue toxicity, incompatibility, instability, irritation, allergic response, and the like.

As used herein, "safe and effective amount" means an amount sufficient to provide the desired benefit at a desired level, but low enough to avoid serious side effects. The safe and effective amount will vary with the area being treated, the age and skin type of the end user, the duration and nature of the treatment, the specific ingredient or composition employed, the particular pharmaceutically-acceptable carrier utilized, and like factors.

As used herein, the term "treating" or "treatment" means the treatment (e.g., alleviation or elimination of symptoms and/or cure) and/or prevention or inhibition of a condition (e.g., a skin condition).

What is meant by a "skin condition" is a dermatological disease or disorder including, but not limited to, acne, rosacea, atopic dermatitis, or skin infections and inflammation, or skin characteristic including, but not limited to, pigmentation (e.g., age spots and hyperpigmentation of the skin), hair growth regulation (increase head hair growth), skin texture and smoothness (e.g., wrinkles and fines of the skin), skin firmness, skin elasticity (e.g., puffiness and/or dark circles around the eye), skin vasculature and circulation, cellulite, sebum regulation, and skin shine. Examples of skin infections and inflammations include, but are not limited to, those due to susceptible pathogens such as acne, rosacea, impetigo, folliculitis, furunculosis, eethyma, eczema, psoriasis, atopic dermatitis, herpes, epidermolysis bullosa, iethyosis, and infected traumatic lesions (e.g., ulcers, minor burns, cuts, abrasions, lacerations, wounds, biopsy sites, surgical incisions and insect bites).

The present invention relates to a device for the delivery of electricity (e.g., to induce a desirable biological response) and/or an active agent into a barrier membrane such as skin.

The present device comprises a substrate comprising a plurality of discrete galvanic couples, each galvanic couple comprising a first conductive electrode that is an anode in electronic communication with a second conductive electrode that is a cathode. As used herein, "electronic communication" means that free electrons can directly pass between the first and second conductive electrodes. Electronic communication is distinct from ionic communication. By "ionic communication," it is meant that electrons can pass among elements (e.g., the first and second conductive electrodes, a carrier and the skin) through the migration of ions as "electron movers" in contact with such elements (e.g., electrons pass between the conductive electrodes and the skin via ionic transport of electrolytes, e.g., via the carrier).

In one embodiment, the first and second conductive electrodes are in electronic communication via direct, physical contact with each other. In another embodiment, the first and second conductive electrodes are in electronic communication via at least one conductive material, preferably an inert conductive material. Preferred conductive materials include, but are not limited to, silver, copper and conductive carbon or graphite.

In one embodiment, the device also comprises a carrier and the first and second conductive electrodes are in ionic communication with the carrier, which preferably contains an electrolyte (e.g., ions of one or more electrolytes in the carrier are in contact with the first and second conductive electrodes). The carrier is in turn in ionic communication with the skin.

In another embodiment, the device is a booster patch. Such booster patch may be placed directly against the skin. Alternatively, such booster patch may be used in conjunction with a facial mask, for example. The facial mask and booster patch are applied together to the skin. The device overlays or underlies the facial mask. Such facial mask may of a conventional type, i.e., a wet or dry facial mask containing various skin benefit agents and vehicles. Alternatively, the facial mask may additionally comprise conductive electrodes for the administration of electricity or delivery of active agents. Such conductive electrodes may be of the galvanic type, or may be connected to a separate power source, as described for example in US Patent Application Publication No. US2007/0060862, the contents of which are hereby incorporated by reference in their entirety.

In one embodiment, the device contains a light emitting diode such that light from the light emitting diode is in communication with the skin. In this manner, light may also be administered to the skin.

In one embodiment, the device delivers an active agent to the skin. The active agent may be incorporated in the substrate, the carrier, separately deposited on skin, or electrochemically generated by the device during use. As used herein, "electrochemically generated" means created as a result of the electrochemical reaction resulting from electric current flowing through a conductive electrode, such a chemical specie released from a reactive conductive electrode (e.g., an electrochemically generated zinc ion from a zinc electrode), a chemical specie electrochemically generated on the surface of an inert electrode, or a chemical specie that is a subsequent reaction product of such electrochemically generated specie.

Galvanic Couple

The device comprises at least two discrete, galvanic couples as power sources. Preferably the device comprises at least 2, more preferably at least 4 discrete galvanic couples. Each galvanic couple comprises a first conductive electrode that is an anode and a second conductive electrode that is a cathode. The first and second conductive electrodes are in physical contact with one another. Electrons pass between the first and second conductive electrodes of each galvanic couple. The electrons are generated as a result of the difference in the standard potentials of the first and second conductive electrodes (e.g., the electricity is not generated by an external battery or other power source such as an AC power source).

Examples of materials that provide galvanic couples include, but are not limited to, zinc-copper, zinc-copper/copper halide, zinc-copper/copper oxide, magnesium-copper, magnesium-copper/copper halide, zinc-silver, zinc-silver/silver oxide, zinc-silver/silver halide, zinc-silver/silver chloride, zinc-silver/silver bromide, zinc-silver/silver iodide, zinc-silver/silver fluoride, zinc-gold, magnesium-gold, aluminum-gold, magnesium-silver, magnesium-silver/silver oxide, magnesium-silver/silver halide, magnesium-silver/silver chloride, magnesium-silver/silver bromide, magnesium-silver/silver iodide, magnesium-silver/silver fluoride, magnesium-gold, aluminum-copper, aluminum-silver, aluminum-silver/silver oxide, aluminum-silver/silver halide, aluminum-silver/silver chloride, aluminum-silver/silver bromide, aluminum-silver/silver iodide, aluminum-silver/silver fluoride, copper-silver/silver halide, copper-silver/silver chloride, copper-silver/silver bromide, copper-silver/silver iodide, copper-silver/silver fluoride, iron-copper, iron-copper/copper oxide, iron-copper/copper halide, iron-silver, iron-silver/silver oxide, iron-silver/silver halide, iron-silver/silver chloride, iron-silver/silver bromide, iron-silver/silver iodide, iron-silver/silver fluoride, iron-gold, iron-conductive carbon, zinc-conductive carbon, copper-conductive carbon, magnesium-conductive carbon, and aluminum-carbon. The materials which serve to make up the galvanic couple may also serve as the conductive electrodes of the device, e.g., zinc as the conductive anode and silver/silver chloride as the conductive cathode or zinc as the conductive anode and copper as the conductive cathode. The metals that serve as the conductive electrodes may also be alloys. Non-limiting examples of the alloys include alloys of zinc, copper, aluminum, magnesium as anode materials, and alloys of silver, copper, gold as cathode materials.

In one embodiment, the first conductive electrode comprises zinc, magnesium, iron, aluminum, alloys thereof, or mixtures thereof, and the second conductive electrode comprises copper, iron, gold, silver, platinum, carbon, alloys thereof, oxides thereof, halides thereof, or mixtures thereof.

In one embodiment, one or more conductive materials may be incorporated into either or both of the first conductive electrode and the second conductive electrode to increase electrode conductivity.

In one embodiment, the materials that make up the galvanic couple have a standard potential difference equal to or greater than about 0.1 volts, such as greater than about 0.2 volts such as greater than about 0.5 volts. In one embodiment, the materials that make up the galvanic couple have a standard potential difference equal to or less than about 3 volts.

Electric current output of each galvanic couple may vary depending on the treatment duration and the size of the galvanic couple. In general, for longer treatment durations, a lower current output may be used. In addition, the larger the size of the galvanic couple, the higher the current output.

In one embodiment, the device generates and/or is capable of generating current into the skin or other barrier membrane of from about 1 nano-A/$cm^2$ to about 1000 micro-A/$cm^2$ of electricity, such as from about 1 micro-A/$cm^2$ to about 500 micro A/$cm^2$.

In another embodiment, in particular for the treatment of pain, the total current penetrating through the skin provided by a device consisting a single galvanic couple or a plurality of galvanic couples may be about 20 to about 2000 micro-A, preferably from about 50 micro-A to about 1000 micro-A, and more preferably from about 100 micro-A and 500 micro-A.

The conductive electrodes may be applied to the substrate using any one of a variety of deposition techniques known in the art. For example, one or both of the first and second conductive electrodes may be a piece of metal sheet, wire or mesh, or a metal-coated fabric or other material such as a fabric coated with a metal, and its oxide, halide, and sulfide, such as a fabric coated with silver, silver/silver oxide, silver/silver halide, zinc, magnesium, copper, copper/copper halide, copper/copper oxide. Such material may optionally be perforated. For example, zinc mesh (or "expanded zinc" as common called in battery and anti-corrosion fields) may be prepared from a thin zinc foil with mechanical perforation and subsequent expansion into net-like patterns. The major advantages of zinc mesh or other mesh are its ability to form and retain shapes, stretch in any direction, and breathe.

Alternatively, the first and second conductive electrodes may be deposited on the substrate by chemical or electrochemical deposition such as electroless plating for chemical deposition and electroplating for electrochemical deposition as known in the art. The first and second conductive electrodes may be deposited on the substrate by physical deposition, such as screen printing, spray coating, gravure printing, laser jet printing, pad printing, needle printing, dip coating, vacuum deposition, or other printing or transfer processes.

In one embodiment, conductive electrodes may be created by formulating galvanic materials into inks specific to the process by which the materials are deposited, such as screen printing ink for screen printing or laser jet printing ink for laser jet printing, and may contain ingredients such as solvents, binders, or plasticizers. These formulations must be pharmaceutically acceptable upon drying, i.e., all nonvolatile ingredients must be safe for contact with a barrier membrane. Binders may include those which are water soluble and water insoluble. Examples of pharmaceutically accepted binders include but are not limited to polyethylene, polypropylene, polyvinylchloride, polystyrene, acrylonitrile butadiene styrene, poly (ethylene terephthalate), polyurethane, hydroxypropyl methylcellulose, polyvinyl pyrrolidone, polyethyleneglycol, hydroxypropyl cellulose, hydroxyethyl cellulose, methylcellulose, poloxamers, and reverse poloxamers.

The size of the galvanic couples may vary according to the device's application. In one embodiment where the device is used for beauty treatment, each galvanic couple occupies an area no greater than about 4 $cm^2$, for instance a 2 cm×2 cm square. In a more preferred embodiment each galvanic couple occupies an area no greater than about 1 $cm^2$, for example a 1 cm by 1 cm square. The overall dimensions of each galvanic couple may vary from about 0.01 $cm^2$ to about 10 $cm^2$.

In an alternate embodiment where the device is used for pain treatment, larger electrodes which provide longer lasting current treatment as well as potentially higher levels of current may be used. Each galvanic couple occupies an area of about 10 to about 400 $cm^2$, for instance a 15 cm×15 cm square. In a more preferred embodiment each galvanic couple occupies an area at about 20 to about 200 $cm^2$, for example a 10 cm by 10 cm square. In this embodiment, the overall dimensions of each galvanic couple may vary from about 10 $cm^2$ to about 400 $cm^2$.

The galvanic couples may be arranged in many ways, provided they are discrete from one another, that is, the individual galvanic couples are disconnected and do not touch one another. The galvanic couples can be arranged as desired to increase or decrease the density of electricity.

Figure 2:
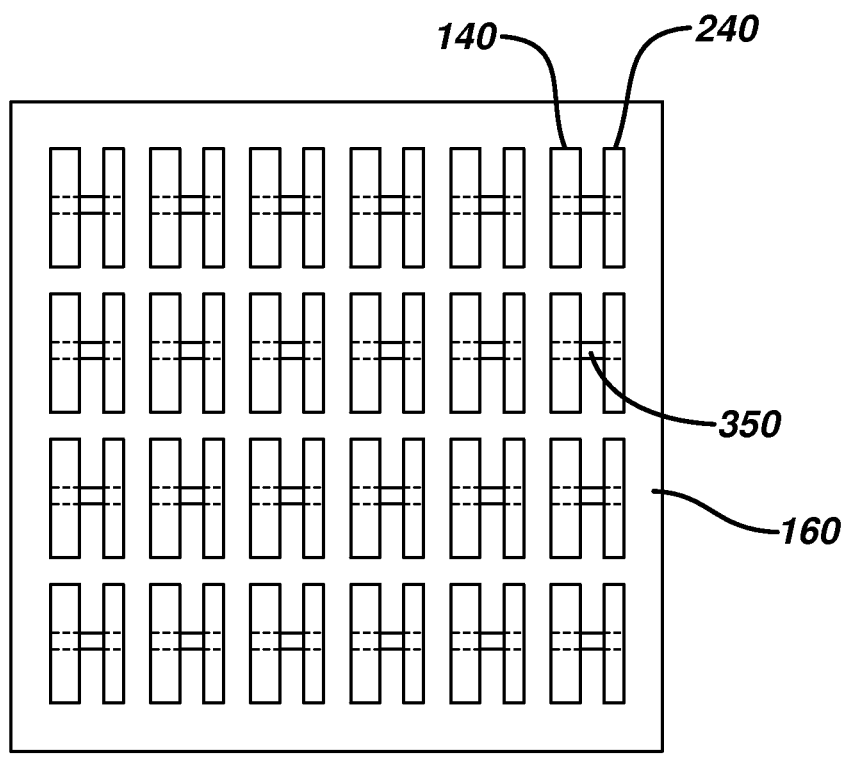
FIG. 2 is a top view of a device according to the invention comprising a substrate 160 comprising a plurality of discrete galvanic couples each comprising a first conductive electrode 140 and a second conductive electrode 240 brought into electrical communication by a connecting bridge comprising a conductive material 350.
Figure 4:
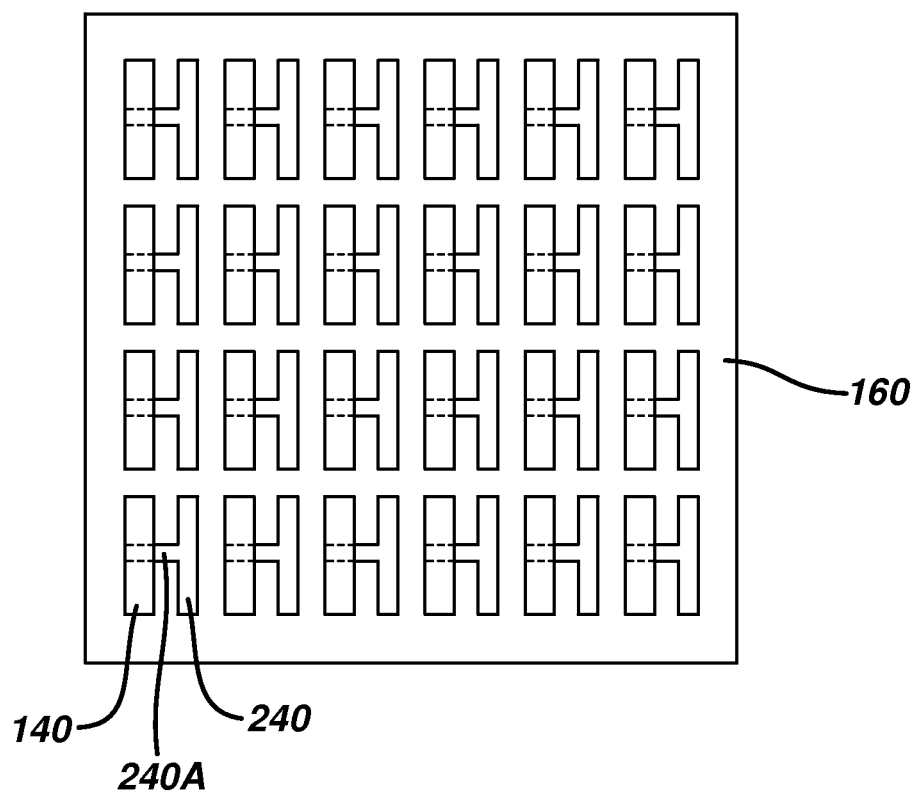
FIG. 4 is a top view a device according to the invention comprising a substrate 160 comprising a plurality of discrete galvanic couples each comprising a first conductive electrode 140 and a second conductive electrode 240 brought into electrical communication by a connecting bridge comprising an extension of the second conductive electrode 240A.
Figure 6:
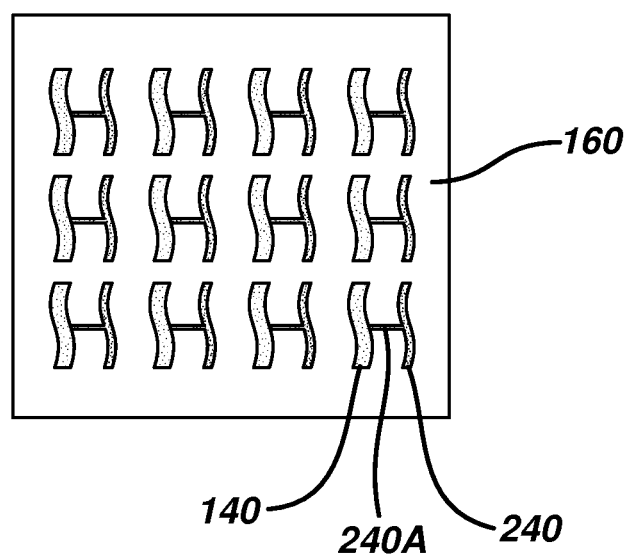
FIG. 6 is a top view of a device according to the invention comprising a plurality of discrete galvanic couples as shown in FIG. 5.
Figure 8:
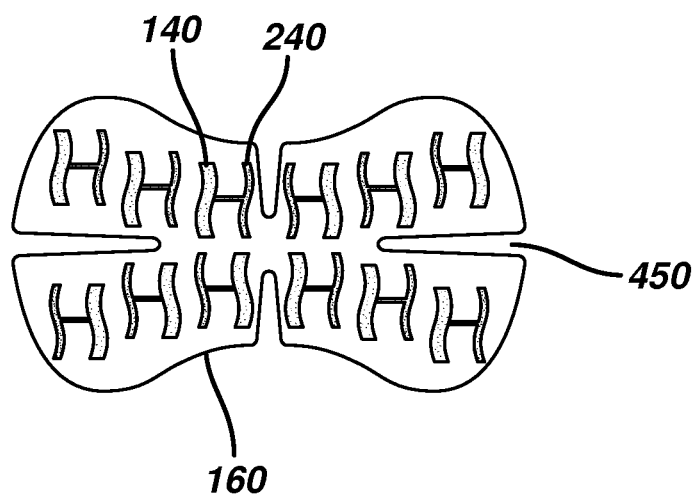
FIG. 8 is a top view of a device according to the invention for use as a booster patch. Relief slits 450 are incorporated into the periphery of the booster patch to enhance its ability to conform to skin surfaces.

In one embodiment, the galvanic couples are evenly spaced from one another, for example in regular or repeating pattern on the substrate, as shown in FIGS. 2, 4 and 6. In another embodiment, the galvanic couples are irregularly spaced on the substrate, as shown in FIG. 8. In another embodiment, the galvanic couples may be spaced on the substrate to form a design, pattern, logo, or letters on the substrate.

Figure 7:
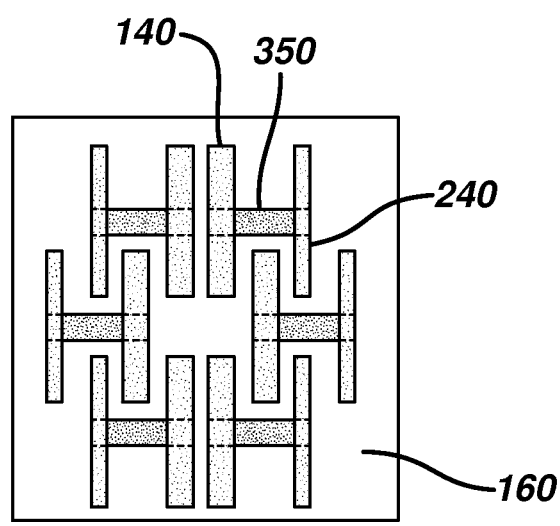
FIG. 7 is a top view of a device according to the invention comprising a plurality of discrete galvanic couples as shown in FIG. 1 in a nested configuration.

In one embodiment, the galvanic couples are nested such that they overlap each other's perimeter. One example of nested galvanic couples is shown in FIG. 7.

In one embodiment galvanic couples can be oriented to focus cathodic or anodic treatment towards a point on the substrate to magnify the effect of such cathode or anode.

Alternatively, the galvanic couples may be arranged on the substrate to best suit the intended treatment.

A single galvanic couple may be employed, or a plurality of galvanic couples in an array may be used. The orientation of galvanic couples in an array may be in any direction relative to one another, or the galvanic couples may be arranged in certain patterns, for example, in parallel or non-parallel arrays, as well as crossed or nested patterns, to encompass the some or all or the intended area of treatment.

Electrode spacing will depend on application. Electric current penetrates deeper into the tissues with increased electrode spacing. Electrodes placed too close together may not deliver current deep into the tissues, where pain originates. In one embodiment, in the case of back pain, the device will be designed such that electrodes of the galvanic couples are spaced across the area of pain. For example, for treatment of back pain the electrodes would preferably be placed at least 5 cm apart, more preferably at least 10 cm apart.

In one embodiment, for knee pain, galvanic couples may be spaced to cover opposite sides of the knee.

In any case, use of a plurality of galvanic couples on the substrate enables the tailored distribution of multiple positive and negative poles over a treatment area. This is not possible with conventional electrical devices that offer only anode and one cathode, or devices that contain scattered metallic particles. Because each galvanic couple acts independently of surrounding ones, each galvanic couple exclusively treats the skin directly adjacent to it to deliver an even dose of electricity to the treatment area.

Another advantage of this effect is that the maximum dose of electricity is controlled by the output of each galvanic couple. This is particularly advantageous if a portion of the treatment area has varying conductivity or compromised skin integrity, such as with a wound (e.g. the maximum current supplied is limited to that provided by the local galvanic couples only).

The first and second conductive electrodes may be arranged in many ways within each galvanic couple. Preferably, the first and second conductive electrodes are arranged in equidistant traces (i.e. fixed distance between anode and cathode along a single Cartesian axis) such that current distribution between the electrodes is uniform. Preferably the gap between a first conductive electrode that is an anode and a second conductive electrode that is a cathode is equal to, or on the order of the gap between adjacent galvanic couples to evenly distribute current delivered to the skin.

Anode and cathode traces (first and second conductive electrodes) must be in electronic communication for galvanic current to be generated. In other words, the first and second conductive electrodes must be electronically bridged by a medium that readily conducts transit of free electrons, such as a metal or carbon.

In one embodiment, the first and second conductive electrodes are in contact through a connecting bridge comprising a conductive material, for example an inert conductive material such as but not limited to silver or carbon.

In another embodiment, the first and second conductive electrodes are in contract through a connecting bridge comprising an extension of the first conductive electrode, the second conductive electrode, or both.

Preferably, the connecting bridge is as thin as possible without losing conductivity, such that electrochemical reaction along the bridge is limited. The minimum achievable thickness for connecting bridges depends on the deposition process. For example, a trace thickness of 0.1 mm can be achieved in screen printing. It is preferred that the connecting bridge have a thickness of about 0.01 to about 10 mm and more preferably from about 0.1 to about 2.0 mm.

The connecting bridge serves an important role in the performance of the galvanic couple in that it may act as an electric resistor and regulate electrical current. Thus, the magnitude and duration of the electric current may be controlled by modulating the resistance provided by the connecting bridge. The resistance of the connecting bridge may be controlled by varying connecting bridge material conductivity as well as geometric parameters of the connecting bridge. Longer and narrower connecting bridges offer greater electrical resistance than shorter, wider connecting bridges.

In one embodiment, connecting bridges may comprise wavy or zigzag patterns with longer path-length than a straight line provides, thus increasing the connecting bridge resistance. In one embodiment, the connecting bridge may be situated outside of the space between electrodes. In one embodiment, the connecting bridge may connect the outer edges of the first and second conductive electrodes, such that it is positioned outside the space between electrodes.

In one embodiment, a galvanic couple comprises more than one connecting bridge.

In one embodiment the connecting bridge is situated horizontally between parallel first and second conductive electrodes such that the galvanic couple is substantially H-shaped. In another embodiment the connecting bridge is situated horizontally between parallel first and second electrodes such that the galvanic couple is substantially U-shaped. In another embodiment, the connecting bridge is situated diagonally between first and second conductive electrodes such that the galvanic couple is substantially N-shaped. The connecting bridge can be placed in any orientation or have any shape such that the first and second conductive electrodes are brought into electrical communication. It is preferred that the bridge provide electrical resistances in the range of 0.1-1,000,000 ohms depending on desired electrical current.

A symmetric galvanic couple design has the advantage of uniform distribution of resulting electric field and electric current. However, an asymmetric design may also be made by either moving the connecting bridge up or down (i.e., moving away from the middle position of the vertical legs to achieve non-uniform electricity distribution. In general, the shape or location or the length/width of the horizontal connecting bridge may be designed to achieve desirable electric current intensity and distribution, for example making it tilted to form an "N" instead of an "H". Alternatively, the relative location of the first and second conductive electrodes of the "H" may also be changed to provide asymmetry and achieve a non-uniform electric distribution.

Individual galvanic couples act independently of surrounding galvanic couples. Therefore, a substrate comprising an array of galvanic couples can be cut to smaller parts without loss of activity provided at least some individual galvanic couples remain intact on the resulting pieces of substrate.

Accordingly, in one embodiment the device may be constructed such that a user can cut the device into multiple, smaller sections in order to personalize the device or custom fit the user's skin.

Electrical current specifications for the device, such as current intensity, current density, and current duration, may vary based on intended benefit.

For example, different applications may require varying treatment times. Pimple treatment may require only 20 minutes, whereas wound treatment should be done for 24 hours or longer, and the duration for pain or other sensory discomfort may range from 20 minutes to 48 hours Therefore, control of electrical output is imperative in designing a device for a specific application. Control of electrical current delivered by a galvanic couple may be achieved by several means. Duration and intensity of electrical output can be controlled by modulating the following parameters: amount of anodic and cathodic material deposited as the first and second conductive electrodes, resistances of the first and second conductive electrodes and the connecting bridge, gap width between first and second conductive electrodes, conductivity of carrier added, volume of carrier added, and absorbency of the substrate or other materials adjacent to the device. For inks that have undesirably low conductivity, overall conductivity of a conductive electrode made from such an ink can be enhanced by printing a conductive layer, which is preferably chemically inert, under the trace of the conductive electrode.

Because the electrical current generated by a galvanic couple originates from an electrochemical reaction, there is a potential for pH change at each electrode. pH tends to increase at a cathode and decrease at an anode. Because the rate of pH change depends on the magnitude of electrical current, in certain embodiments, it may be desirable to design a galvanic couple with a self shut-down or self slow-down mechanism to terminate or slow down the rate of pH change once pH levels exceed a desired range. This can be achieved by formulating the first and/or second conductive electrodes to include pH dependent polymers that swell at well defined pH ranges. Such polymers will expand once pH reaches a specific value and reduce electrical conductivity along the electrodes, hindering the electrochemical reaction. pH dependent swelling polymers include but are not limited to polyacrylic acids such as Eudragit S, Eudragit L, Eudragit FS, and Eudragit E which swell in basic environments, and chitosan, which swells in acidic environments.

The first and second conductive electrodes may be reactive conductive electrodes or inert conductive electrodes. A "reactive conductive electrode" is an electrode that undergoes a change in its chemical composition via electrode chemical reactions that occur when electric current passes through the electrode. In one embodiment, the reactive conductive electrode is an anode made of reactive materials such as a pure metal or a metal alloy including, but not limited to, zinc, aluminum, copper, magnesium, manganese, silver, titanium, tin, iron, and alloys thereof. The materials which serve to make up the galvanic couple described earlier may also serve as the reactive conductive electrode. Metal ions such as zinc, copper, magnesium, manganese and/or aluminum cations are released from the anode upon passage of an electric current through each anode into the carrier, and delivered into the skin. Such ions may serve therapeutic benefits such as antimicrobial effects, immunologic modulation, enzymatic regulation, and/or anti-inflammatory effects.

In one embodiment, a reactive conductive electrode is made of reactive materials such as metal halides (e.g., silver-silver chloride (Ag/AgCl), silver-silver bromide, and silver-silver iodide). In this case, the primary electrochemical reaction at the cathode surface is conversion of solid silver halide to metallic silver with little unwanted consumption of the oxidizing agents generated by the anode. The released halide ions may be subsequently oxidized to oxidizing agents, such as chloride ions to chlorine ($Cl_2$), hypochlorous acid (HClO), and hypochlorite ions ($ClO^-$), and iodide ions to iodine.

An "inert conductive electrode" does not undergo a change in its chemical composition during passage of electrons through it. In one embodiment, an anode is made of an inert conductive electrode, so that the electrochemical process at the surface of the anode generates oxidizing agents such as nascent oxygen (e.g., by electrolysis of water) and/or chlorine-containing oxidizing agents such as chlorine, hypochlorite, chlorate and perchlorate, and chlorine dioxide. Nascent oxygen is an oxidizing agent that is inhibitive to *P. acnes*, and chlorine-containing oxidizing agents are potent antimicrobial agent with bactericidal activity.

In one embodiment, a conductive electrode is made of, or coated on the surface with, an inert material such as a noble metal (e.g., gold, platinum, or gold-coated conductive metals), conductive carbon (e.g., glassy carbon or graphite), carbon-embedded polymers (e.g., carbon silicone rubbers), conductive carbon polymer foam or sponge, silver halide-coated silver (e.g., silver chloride-coated silver, silver bromide-coated silver, and silver iodide-coated silver), and corrosive resistant alloys.

In one embodiment, the anode of the device, serving as the first conductive electrode, is made of aforementioned reactive conductive oxidizable metals such as zinc, calcium, magnesium, aluminum, iron, tin, copper, or alloys thereof, while the cathode, serving as the second conductive electrode, is made of the aforementioned reactive reducible conductive materials such as a more chemically stable metal and its metal halides, oxide, sulfide or other metal salts, such as silver and silver halides (e.g., silver chloride, silver bromide, silver iodide, silver fluoride), silver oxide, silver sulfide. In one embodiment, the reducible conductive material is in direct contact with a good electric conductor, such as: a thin layer of silver chloride, silver oxide, or silver sulfide over metallic silver; silver chloride powder with a binder (e.g., silver chloride ink); and/or silver chloride powder mixed with silver or conductive carbon powder held together by a binder in a matrix form (e.g., silver-silver chloride ink and silver chloride-carbon ink).

In another embodiment, the anode of the device is made of aforementioned reactive conductive oxidizable metals while the cathode is made of aforementioned more chemically stable electrode materials such as conductive carbon, metallic silver, gold or platinum, or a powder mixture of conductive carbon and the noble metal in a matrix form as disclosed in U.S. Pat. No. 5,162,043.

In one embodiment, the device of the present invention enables the targeted delivery of beneficial zinc through hair follicles to the pilosebaceous unit (i.e., a sebaceous gland and the associated hair follicle) to treat acne or rosacea. Zinc is an essential metal to the human body because it participates in various biological activities in the body (e.g., the body of a 70-Kg person contains about 2.3 grams of zinc). It is known that the lack of zinc in the body may lead to skin diseases such as acne.

In another embodiment, the device of the present invention enables the targeted delivery of other beneficial metals into the hair follicles and the pilosebaceous glands by using an anode made of zinc alloy containing small quantities of other beneficial metals. Such beneficial metals include, without limitation, certain metals essential to the human body such as iron, copper, magnesium, manganese, calcium, potassium, aluminum, and selenium. As the zinc alloy anode oxidizes, it releases into the carrier zinc ions and other beneficial metals in the zinc alloy, which ingredients subsequently migrate into the hair follicles under the applied electric potential over the skin. In one embodiment, the content of the zinc alloy in the anode is greater than about 50% by weight, such as greater than 90% by weight.

In one embodiment, the ratio of the conductance measured between the first and second conductive electrodes of (i) the carrier and (ii) the skin hydrated with such carrier (wherein substantially all of the current passes between the electrodes through the skin) is in a range from about 10000:1 to about 1:100. In other words, the electric current distribution between $I_{carrier}$ and $I_{skin}$ is such that the value of $I_{carrier}/I_{skin}$ is between about 10,000 and about 0.01. $I_{carrier}$ is the portion of the total current going through the device ($I_{total}$) that only passes through the carrier layer between the anode and cathode without traveling through the skin, whereas $I_{skin}$ is the portion of $I_{total}$ that passes through the skin, namely, $I_{total}=I_{carrier}+I_{skin}$.

Decreasing the ratio of the conductance of the carrier to the conductance of the skin will result in a greater percentage of current passage through the skin, thereby enhancing iontophoretic delivery of any active agents being so delivered into the skin. Decreasing the conductivity of the carrier can non-exclusively be accomplished by adding less conductive materials to the carrier. Examples of such less conductive materials include, but are not limited to, oils such as silicone or hydrocarbon oils, air pockets such as air bubbles or air pockets in a semi-solid carrier, or polymer or clay beads. In one embodiment where the primary intention is to electrochemically generate species in the carrier, the value of $I_{carrier}/I_{skin}$ is between about 10,000 and about 1. In another embodiment where the primary intention is to deliver electricity and/or active agents into the skin, the value of $I_{carrier}/I_{skin}$ is between about 10 and about 0.01. Adjustment of the value of $I_{carrier}/I_{skin}$ for a particular application can also be achieved by changing the distance between the first and the second electrode, or the distance between the two conductive electrodes and the skin. For example, as the distance between the two conductive electrodes decreases, the conductance measured between the two electrode increases and so is the $I_{carrier}$, leading to an increased value of $I_{carrier}/I_{skin}$. On the other hand, if the distance between the two conductive electrodes and the skin increases, the $I_{skin}$ increases, leading to decreased value of $I_{carrier}/I_{skin}$.

Substrate

The device comprises a substrate, on or in which the galvanic couples are situated. The substrate may be fabricated into various shapes and sizes to fit the contours of various anatomical surfaces of the skin or other barrier membranes. For example, the substrate made in the shape of a whole facial mask with openings/holes to expose the eyes, eye bows, nose, and mouth; a partial facial mask covering only the upper or lower half of the face; or a patch covering only the forehead, or the under eye region, the chin and jaw region, the neck, the back, wound, acne lesion or pimple, or other specific area of a barrier membrane in need of treatment.

The substrate may be made of a variety of materials, such as paper, plastic or water-insoluble polymer, woven materials (e.g. woven fabric), and non-woven materials (nonwoven fabric). The substrate may comprise "breathable" material such as, but not limited to, a cotton or synthetic woven and nonwoven fabric layer, such as those fabric materials commonly used for bandages and sports bandages. The substrate may comprise electrically conductive material, such as electrically conductive plastic, woven, nonwoven, or paper.

In one embodiment, the substrate comprises a fluid-absorbing material for example a material usually regarded as paper, including but not limited to tissue paper, filter paper, copy paper, bond paper, hydrogen bonded paper, paper from groundwood stock, paper from fiber pulp, paper made from wood pulp, paper made from nonwood pulp, recycled paper, freesheet paper, papers with coatings including but not limited to acrylic coating, silicone coating, calcderized paper, papers with additives such as but not limited to Kymene® to enhance wet strength, papers with low molecular weight polyacrylamide additives to enhance dry strength, papers with water soluble or water-insoluble binder to increase mechanical strength, printability and ease of handling, papers including pigments, absorbent papers, or papers composed of electrically conductive fibers. The paper should be safe for application to human skin, and the components of the paper should be non-toxic, non-irritating and non-sensitizing to the skin. The paper may be electrically conductive or non-conductive.

For manufacturability it is preferable that the paper is sufficiently rigid when dry such that it can be easily handled and processed during printing of the galvanic couples thereon, but loses rigidity greatly during use, upon wetting by the user, so that it can readily conform and adhere to barrier membrane (e.g., the skin) Barrier membrane contacting surface conformability and ability to contact anatomical contours is particularly important for treatment of barrier membranes with sharp curvature of certain anatomic features, such as the skin around the cheekbone or nose. Upon wetting, these surfaces must provide adequate flexibility and conformability to adapt to the skin while maintaining a certain structural integrity such that they are not vulnerable to tearing or disintegration upon use.

In one embodiment the fluid absorbing material may be treated to prevent or retard water evaporation during use. For example, nonwoven material or paper may be silicon coated on one side to form a water impermeable barrier.

Examples of fluid-absorbing materials include, but are not limited to: cross-linked and non-cross-linked polymers; swellable polymers such as water-swollen cellulose derivatives (e.g., methylcellulose (MC), hydroxyethyl methylcellulose (HEMA), hydroxypropyl methylcellulose (HPMC), ethylhydroxyethyl cellulose (EHEC), hydroxyethylcellulose (HEC), hydroxypropylcellulose (HPC), and carboxymethlcellulose (CMC) and their salts); polyvinyl alcohol (PVA); polyvinylpyrrolidone (PVP); polyethylene oxide (PEO); polymers prepared by monomers such as hydroxyethyl methacrylate (HEMA), hydroxyethoxyethyl methacrylate (HEEMA), hydroxydiethoxyethyl methacrylate (HDEEMA), methyoxyethyl methacrylate (MEMA), methoxyethoxyethyl methacrylate (MEEMA), methyldiethoxyethyl methacrylate (MDEEMA), ethylene glycol dimethacrylate (EGDMA), n-vinyl-2pyrrolidone (NVP), methacrylic acid (MA), and vinyl acetate (VAC); polyacrylamide; gelatin; gums and polysaccharides such as gum arabic, gum karaya, gum tragacanth, guar gum, gum benzoin, and alginic acid and their salts; polyethylene glycol (PEG); polypropylene glycol (PPG); and clays or other swellable minerals such as bentonite and montmorillonite. The amount of fluid absorbable material in the carrier may range from about 0.1% to about 95%, by weight, such as from about 1% to about 20%, by weight, of the carrier.

In one embodiment of the present invention, the substrate comprises a water-insoluble substrate. By "water insoluble" it is meant that the substrate, upon immersion in distilled water at 25° C., does not readily dissolve in or readily break apart. The water-insoluble substrate may, however, be disintegrated and/or dissolved slowly, i.e., over a period of several hours up to several days. A wide variety of materials can be used as the water-insoluble substrate. Examples of suitable substrates include, but are not limited to, non-woven substrates, woven substrates, hydro-entangled substrates, air entangled substrates, natural sponges, synthetic sponges, and polymeric netted meshes.

The water insoluble substrates may be flushable. As used herein, by "flushable" it is meant that the substrate will pass through at least 10 feet of waste pipe in two toilet flushes. The material may also be biodegradable.

In one embodiment, the substrate contains a non-woven material. By "non-woven" it is meant that the substrate, or a layer of the substrate, is comprised of fibers that are not woven into a fabric but rather are formed into a sheet, mat, or pad layer. The fibers can either be random (i.e., randomly aligned) or they can be carded (i.e., combed to be oriented in primarily one direction. Furthermore, the non-woven substrate can be composed of a combination of layers of random and carded fibers).

Non-woven substrates may be comprised of a variety of natural and/or synthetic materials. By "natural" it is meant that the materials are derived from plants, animals, insects, or byproducts of plants, animals, and insects. By "synthetic" it is meant that the materials are obtained primarily from various man-made materials or from natural materials, which have been further altered. Non-limiting examples of natural materials useful in the present invention are silk fibers, keratin fibers (such as wool fibers, camel hair fibers) and cellulosic fibers (such as wood pulp fibers, cotton fibers, hemp fibers, jute fibers, and flax fibers).

Examples of synthetic materials include, but are not limited to, those selected from the group containing acetate fibers, acrylic fibers, cellulose ester fibers, cotton fibers, modacrylic fibers, polyamide fibers, polyester fibers, polyolefin fibers, polyvinyl alcohol fibers, rayon fibers, polyurethane foam, and mixtures thereof.

Substrates made from one or more of the natural and synthetic materials useful in the present invention can be obtained from a wide variety of commercial sources such as Freudenberg & Co. (Durham, N.C. USA), BBA Nonwovens (Nashville, Tenn. USA), PGI Nonwovens (North Charleston, S.C. USA), Buckeye Technologies/Walkisoft (Memphis, Tenn. USA), and Fort James Corporation (Deerfield, Ill. USA).

Methods of making non-woven substrates are also well known in the art. Such methods include, but are not limited to, air-laying, water-laying, melt-blowing, spin-bonding, or carding processes. The resulting substrate, regardless of its method of production or composition, is then subjected to at least one of several types of bonding operations to anchor the individual fibers together to form a self-sustaining web. The non-woven substrate can be prepared by a variety of processes including hydro-entanglement, thermally bonding, and combinations of these processes. Moreover, the substrates can have a single layer or multiple layers. In addition, a multi-layered substrate can include film layer(s) (e.g., aperture or non-aperture film layers) and other non-fibrous materials.

Strength or firmness of the non-woven material may be a desirable attribute. This can be achieved, for example, by the addition of binding materials, such as wet strength resins, or the material may be made of polymer binder coatings, stable fibers, e.g. based on cotton, wool, linen and the like. Examples of wet strength resins include, but are not limited to, vinyl acetate-ethylene (VAE) and ethylene-vinyl chloride (EVCL) Airflex emulsions (Air Products, Lehigh, Pa.), Flex-bond acrylic polymers (Air Products, Lehigh, Pa.), Rhoplex ST-954 acrylic binder (Rohm and Haas, Philadelphia, Pa.), and Ethylene-vinyl acetate (EVA) emulsion (DUR-O-SET® by National Starch Chemicals, Bridgewater, N.J.). The amount of binding material in the substrate may range from about 5% to about 20%, by weight, of the substrate.

Non-woven materials of increased strength can also be obtained by using the so-called spunlace or hydro-entanglement technique. In this technique, the individual fibers are twisted together so that an acceptable strength or firmness is obtained without the need to use binding materials. The advantage of the latter technique is the excellent softness of the non-woven material.

In one embodiment, the non-woven material comprises a superabsorbent polymer. For the purposes of the present invention, the term "superabsorbent polymer" refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and other material known to the art of absorbent article manufacture.

Active agents may also be incorporated into the substrate during manufacturing processes or be subsequently applied to the substrate prior to the application to the barrier membrane (e.g., in the form of an electrolyte or active agent containing liquid spray to wet the substrate).

Additives may also be added in order to increase the softness of the substrates. Examples of such additives include, but are not limited to, polyols such as glycerol, propylene glycol and polyethylene glycol, phthalate derivatives, citric esters, surfactants such as polyoxyethylene (20) sorbitan esters, and acetylated monoglycerides.

Sensory attributes may also be incorporated the substrate. Examples of such sensory attributes include, but are not limited to color, texture, pattern, and embossing.

Carrier

The device optionally includes a carrier. The carrier may be a liquid (e.g., a solution, a suspension, or an emulsion which optionally may be immobilized within an absorbent material such as gauze or non-woven pad), a semi-solid (e.g., a gel, a cream, a lotion, microemulsion, or hydrogel), or a solid (e.g., a lyophilized composition optionally containing active agents, which may be reconstituted by adding a liquid prior to use) that during use is capable of conducting electricity from a conducting electrode (e.g., the carrier contains one or more electrolytes, organic solvents, and water). In one embodiment, the carrier (e.g., a liquid or semi-solid) is added to the device by the user prior to applying the device to the skin. In another embodiment, the carrier is first applied to the skin, followed by application of the device.

In one embodiment, the carrier is present in at least about 50%, such as at least about 75%, by weight of the total weight of the substrate prior to use. In another embodiment, a liquid carrier is present in less than about 10%, such as less than about 1%, by weight of the total weight of a water insoluble substrate (for example, the device may not contain any carrier prior to use). In a further embodiment, the product contains instructions for the user to either (i) wet the substrate prior to application or (ii) wet the barrier membrane (e.g., the skin) with water and/or another liquid prior to application.

Examples of electrolytes for use in the carrier include, but are not limited to, pharmaceutically acceptable organic and organic salts and buffers. Examples of salts include, but are not limited to, chloride salts (such as sodium chloride, potassium chloride, lithium chloride, calcium chloride, strontium chloride, magnesium chloride or other chloride salts), as well as salts of sodium, potassium, lithium, calcium, magnesium, strontium, fluoride, iodide, bromide. Examples of buffers include, but are not limited to, phosphates, citrates, acetates, lactates, and borates.

In one embodiment, the electrolyte is an active agent, or becomes an active agent after the passage of the electric current through the carrier. Examples of such electrolyte-active agents include, but are not limited to, salicylic acid, salicylates, and other weak acid or weak base active agents.

In one embodiment, the carrier is or contains water. In a further embodiment, the carrier may also contain one or more organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols.

Examples of glycols include, but are not limited to, glycerin, propylene glycol, butylene glycol, pentalene glycol, hexylene glycol, polyethylene glycol, polypropylene glycol, diethylene glycol, triethylene glycol, glycerol, and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol.

Organic solvents may be present in the carrier in an amount, based upon the total weight of the carrier, of from about 1 percent to about 90 percent (e.g., from about 5 percent to about 50 weight percent of the carrier). Water may be present in the carrier (prior to use) in an amount, based upon the total weight of the carrier, of from about 5 percent to about 95 percent (e.g., from about 50 percent to about 90 percent).

The carrier may also contain: preservatives (such as cresol, chlorocresol, benzyl alcohol, methyl p-hydroxylbenzoate, propyl p-hydroxybenzoate, phenol, thimerosal, benzalkonium chloride, benzethonium chloride, and phenylmercuric nitrate); stabilizing agents or antioxidants (such as ascorbic acid, ascorbic acid esters, butylhydroxy anisole, butylhydroxy toluene, cysteine, N-acetylcysteine, sodium bisulfite, sodium metabisulfite, sodium formaldehydesulfoxylate, acetone sodium bisulfite, tocopherols, and nordihydroguaiaretic acid); chelating agents (such as ethylenediaminetetraacetic acid and its salts); buffers (such as acetic acid, citric acid, phosphoric acid, glutamic acid, and salts thereof); and tonicity adjusting agents (such as sodium chloride, sodium sulfate, dextrose and glycerin).

In one embodiment, the carrier may also contain a suspending material and/or a fluid-absorbing material (e.g., for physically stabilizing the ingredients of the carrier) such as those described for use in the substrate. In one embodiment, the carrier comprises a fluid-absorbing material comprising paper, such as that described in connection with the substrate. Paper used in the carrier should also be for application to the skin, and the components of the paper should be non-toxic, non-irritating and non-sensitizing to the skin.

Another embodiment of the present invention is directed to pairing one or more inert conductive electrodes in order to electrochemically generate oxidizing or reducing agents from electrochemically reactive materials in situ in the carrier. Such oxidizing or reducing agents can be used as active agents to treat barrier membrane conditions.

Examples of the electrochemically reactive materials in the carrier according to the present invention include, but are not limited to, water and compounds containing the elements selected from the Periodic Table of the Elements VIIB and VIIB (such as oxygen, sulfur, fluorine, chlorine, bromine, and iodine).

In one embodiment, the reactive material reacts with an inert anode to form an oxidizing agent. Examples of such a reactive material includes, but is not limited to, the ions $OH^-$, $Cl^-$, $I^-$, $Br^-$, $SO_3^{2-}$, and $HCO_3^-$. The present device, thus, enables to generation of oxidizing agents, such as nascent oxygen (e.g., singlet oxygen), chlorine and chlorine dioxide gases, which are difficult to formulate in a conventional topical product.

In one embodiment, the reactive material reacts with the inert cathode to form a reducing agent. Examples of such a reactive material includes, but is not limited to, oxidized or disulfide forms of thio-compounds with one or more sulfhydryl functional groups, thio-containing amino acids and their salts or esters, and sulfides. Examples of such thio-compounds include, but are not limited to: thioglycolic acid and its salts, such as thioglycolates of calcium, sodium, strontium, potassium, ammonium, lithium, magnesium, and other metal salts; thioethylene glycol; thioglycerol; thioethanol; thioactic acid; and thiosalicylic acid; and their salts. Examples of the thio-containing amino acids include, but are not limited to, L-cysteine, D-cysteine, DL-cysteine, N-acetyl-L-cysteine, DL-homocysteine, L-cysteine methyl ester, L-cysteine ethyl ester, N-carbamoyl cysteine, glutathione, and cysteamine. Examples of sulfides, include but are not limited to, calcium, sodium, potassium, lithium and strontium sulfides and glutathione disulfide. The inert cathode converts the aforementioned reactive oxidized or disulfide form of a sulfur-containing compound to a thio-containing compound, or a sulfhydryl-containing compound. An example of such a conversion is the conversion of cystine to cysteine and the conversion of the oxidized form of glutathione to glutathione.

In one embodiment, the concentration of the reactive material in the carrier may range from about 0.01% to about 25%, by weight, such as from about 0.1% to about 10%, by weight, of the carrier. The pH value of the carrier may range from about pH 1.5 to about pH 9, preferably from pH 2 to pH 7, and most preferably from about pH 3 to pH 5.

In one embodiment, the carrier or the substrate contains an adhesive. The adhesive may be used to affix the device to the skin. Examples of hydrophobic adhesives include, but are not limited to, silicones, polyisobutylenes and derivatives thereof, acrylics, natural rubbers, and combinations thereof. Examples of silicone adhesives include, but are not limited to, Dow Corning 355 available from Dow Corning of Midland, Mich.; Dow Corning X7-2920; Dow Corning X7-2960; and GE 6574 available from General Electric Company of Waterford, N.Y. Examples of acrylic adhesives include, but are not limited to, vinyl (D acetate-acrylate) multipolymers such as Gelva 7371, available from Monsanto Company of St. Louis, Mo.; Gelva 7881; Gelva 2943; and 1-780 medical grade adhesive available from Avery Dennison of Painesville, Ohio. Examples of hydrophilic adhesives include, but are not limited to, gum papaya and other natural gums, MC, HEMA, HPMC, EHEC, HEC, HPC, CMC, PVA, PVP, PEO, HEMA, HEEMA, HDEEMA, MEMA, MEEMA, MDEEMA, EGDMA, NVP MA, VAC, polyacrylamide, gelatins, gum arabic, gum karaya, gum tragacanth, guar gum, gum benzoin, and alginic acid and their salts, polyethylene glycol (PEG), and polypropylene glycol (PPG).

In one embodiment, the concentration of the adhesive in the carrier may range from about 0.1% to about 95%, by weight, such as from about 1% to about 20%, by weight, of the carrier.

The device may optionally comprise a removable release liner, for example covering a substrate or carrier comprising an adhesive, for example an adhesive hydrogel. The release liner is typically a polymer sheet or a paper or fabric coated with a polymer, which has weak adhesion toward the adhesive hydrogel, thereby allowing it to be easily removed prior to use without damaging the device. Examples of the polymers typically used for the release liner are silicones and polyethylenes. Alternatively, a wax may be used in the place of the polymer to coat the release liner.

In addition to, or in lieu of, the use of an adhesive, the device may be fastened to the skin with an adhesive tape, an elastic band, a band with a buckle (similar to a leather watch band), or a Velcro® band.

In order to use device, the optional removable release liner sheet is peeled off, and optional carrier is placed on the device or the skin of the user. The device may then be directly affixed to the skin.

In another embodiment, the device comprises a backing layer such as an unperforated or perforated polymer film, i.e., polyethylene terephthalate, or an absorbent material such as paper.

One embodiment of the present invention is a dual-pack system, in which the device and the carrier (or a portion of the carrier) are packaged separately. One portion of the carrier may be an anhydrous liquid-immobilizing matrix, such as a dry woven or nonwoven fabric, a sponge, or a dehydrated hydrogel layer (e.g., freeze-dried hydrogel), while the liquid portion of the carrier, such as a solution, gel, or cream containing active agents, is packaged in a separate liquid containing compartment, such as a unit dose pouch, a breakable container or a bottle. Prior to use, the liquid-containing compartment is broken and the liquid or semisolid portion of the carrier is applied to the liquid-immobilizing matrix to activate the current generation for skin application. Active agents are either incorporated into the liquid-immobilizing matrix or the liquid/semisolid composition.

In one embodiment, the device is a self terminating device. The device employs a carrier comprising water. As water in the carrier composition evaporates, the electric conductance and the electric current decrease. Eventually, the electric current significantly diminishes, providing in essence a self-terminating device to serve as a safety measure for the user to prevent any unintentional over-exposure of the skin to the electric current and potential resulting skin damage.

Active Agents

In one embodiment, the substrate or the carrier contains one or more active agents. The active agent may be incorporated into the substrate or carrier as dissolved molecules and ions, dispersed solid particles, or liquid droplets such as cream, lotion, emulsion, multi-emulsion, microemulsion, and/or liposome compositions.

What is meant by an "active agent" is a compound (e.g., a synthetic compound or a compound isolated from a natural source) that has a cosmetic or therapeutic effect on the barrier membrane and the surrounding tissues (e.g., a material capable of exerting a biological effect on a human body) such as therapeutic drugs, including, but not limited to, organic and macromolecular compounds. Examples of such therapeutic drugs include peptides, polypeptides, proteins, and nucleic acid materials comprising DNA; and nutrients. Examples of polypeptide and protein active agents include thyrotropin-releasing hormone (TRH), vasopressin, gonadotropin-releasing hormone (GnRH or LHRH), melanotropin-stimulating hormone (MSH), calcitonin, growth hormone releasing factor (GRF), insulin, erythropoietin (EPO), interferon alpha, interferon beta, oxytocin, captopril, bradykinin, atriopeptin, cholecystokinin, endorphins, nerve growth factor, melanocyte inhibitor-I, gastrin antagonist, somatotatin, encephalins, melatonin, vaccines, botox (Botulinum neurotoxins), cyclosporin and its derivatives (e.g., biologically active fragments or analogs). Other active agents include anesthetics; analgesics (e.g., fentanyl and salts thereof such fentanyl citrate); drugs for treating psychiatric disorders, epilepsies, and migraine; drugs for stopping drug additions and abuses; anti-inflammatory agents; drugs to treat hypertension, cardiovascular diseases, gastric acidity and ulcers; drugs for hormone replacement therapies and contraceptives such as estrogens and androgens; antibiotics, antifungals, antiviral and other antimicrobial agents; antineoplastic agents, immunosuppressive agents and immunostimulants; and drugs acting on blood and the blood forming organs including hematopoietic agents and anticoagulants, thrombolytics, and antiplatelet drugs. Other active agents that can be delivered into the body using the shear device in the present invention include vaccines for various diseases, such as those for influenza, AIDS, hepatitis, measles, mumps, rubella, rabies, rubella, avercella, tetanus, hypogammaglobulinemia, Rh disease, diphtheria, botulism, snakebite, black widow bite and other insect bite/sting, idiopathic thrombocytopenic purpura (ITP), chronic lymphocytic leukemia, cytomegalovirus (CMV) infection, acute renal rejection, oral polio, tuberculosis, pertussis, *Haemophilus* b, *Pneumococcus*, and *Staphylococcus aureus*.

In one embodiment, the substrate or the carrier contains an anti-acne and/or anti-rosacea agent. Examples of anti-acne and anti-rosacea agents include, but are not limited to: retinoids such as tretinoin, isotretinoin, motretinide, adapalene, tazarotene, azelaic acid, and retinol; salicylic acid; benzoyl peroxide; resorcinol; sulfur; sulfacetamide; urea; antibiotics such as tetracycline, clindamycin, metronidazole, and erythromycin; anti-inflammatory agents such as corticosteroids (e.g., hydrocortisone), ibuprofen, naproxen, and hetprofen; and imidazoles such as ketoconazole and elubiol; and salts and prodrugs thereof. Other examples of anti-acne active agents include essential oils, alpha-bisabolol, dipotassium glycyrrhizinate, camphor, β-glucan, allantoin, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and other valences, synthetic phospholipids and natural phospholipids such as Arlasilk™ phospholipids CDM, SV, EFA, PLN, and GLA (Uniqema, ICI Group of Companies, Wilton, UK).

In one embodiment, the device contains an anti-aging agent. Examples of suitable anti-aging agents include, but are not limited to: inorganic sunscreens such as titanium dioxide and zinc oxide; organic sunscreens such as octyl-methoxy cinnamates; retinoids; dimethylaminoathanol (DMAE), copper containing peptides, vitamins such as vitamin E, vitamin A, vitamin C, and vitamin B and vitamin salts or derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccharic acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, dill, blackberry, and safflower; and salts and prodrugs thereof.

In one embodiment, the substrate or carrier contains a depigmentation agent. Examples of suitable depigmentation agents include, but are not limited to: soy extract; soy isoflavones; retinoids such as retinol; kojic acid; kojic dipalmitate; hydroquinone; arbutin; transexamic acid; vitamins such as niacin and vitamin C; azelaic acid; linolenic acid and linoleic acid; placertia; licorice; and extracts such as chamomile and green tea; and salts and prodrugs thereof.

In one embodiment, the substrate or carrier contains a plant extract. Examples of plant extracts include, but are not limited to, feverfew, soy, glycine soja, oatmeal, wheat, aloe vera, cranberry, hazel witch, *alnus, arnica, artemisia capillaris*, asiasarum root, birch, *calendula*, chamomile, cnidium, comfrey, fennel, galla rhois, hawthorn, houttuynia, *hypericum*, jujube, kiwi, licorice, magnolia, olive, peppermint, philodendron, salvia, sasa albo-marginata, natural isoflavonoids, soy isoflavones, and natural essential oils.

In one embodiment, the substrate or carrier contains metals such as metal ions, metal salts, metal complexes, fine metal powders, fine metal coated fibers and fabrics of synthetic or natural origin, or fine metal fibers. Examples of such metals include, but are not limited to, zinc, copper, aluminum, gold, silver, titanium. The metal ions provide benefits such as antimicrobial, anti-inflammatory, and/or sebum-reduction effects. The beneficial metal ions may be released from the metal anode as the result of an electrochemical oxidation reaction concurrent with electric current passage (e.g., zinc ions electrochemically generated from a zinc anode).

In another embodiment, the beneficial ions may be generated indirectly from the electrochemical reactions at the electrode surface, such as the generation of hydrogen or hydroxyl ions at an inert electrode, which subsequently leads to a process to generate beneficial ions. For example, a device of the present invention may contain an inert anode (e.g., platinum, platinum coated conductive electrode, gold, or gold-coated conductive electrode), a reactive cathode (e.g., silver/silver chloride electrode), and an aqueous carrier composition containing an oxide (e.g., zinc oxide particles) among other active agents. During application to the skin, the electrolysis of water at the inert anode produces excess hydrogen ions which acidify the carrier toward a lower pH value, while the electrochemical reaction at the reactive cathode (e.g., the conversion of silver chloride to silver ions) does not affect the pH. As the solution becomes more acidic, the oxide starts to dissolve to release ions (e.g., zinc ions) for their beneficial effects to the barrier membrane.

Other active agents include those commonly used as for topical treatment and in cosmetic treatment of skin tissues, such as topical antibiotics for wounds, topical antifungal drugs to treat fungal infections of the skin and nails, and antipsoriatic drugs to treat psoriatic lesions of the skin and psoriatic nails.

Examples of antifungal drugs include but are not limited to miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs. In one embodiment, the antifungal drugs are an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline-10 hydrochloride and tetrachcycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs.

Examples of antimicrobials include but are not limited to salts of chlorhexidine, such as Iodopropynyl butylcarbamate, diazolidinyl urea, chlorhexidene digluconate, chlorhexidene acetate, chlorhexidene isethionate, and chlorhexidene hydrochloride. Other cationic antimicrobials may also be used, such as benzalkonium chloride, benzethonium chloride, triclocarbon, polyhexamethylene biguanide, cetylpyridium chloride, methyl and benzothonium chloride. Other antimicrobials include, but are not limited to: halogenated phenolic compounds, such as 2,4,4',-trichloro-2-hydroxy diphenyl ether (Triclosan); parachlorometa xylenol (PCMX); and short chain alcohols, such as ethanol, propanol, and the like. In one embodiment, the alcohol is preferably at a low concentration (e.g., less than about 10% by weight of the carrier, such as less than 5% by weight of the carrier) so that it does not cause undue drying of the barrier membrane.

Examples of antipsoriatic drugs or drugs for seborrheic dermatitis treatment include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, hydrocortisone, sulfur, menthol, and pramoxine hydrochloride, and salts and prodrugs thereof.

Examples of anti-viral agents for viral infections such as herpes and hepatitis, include, but are not limited to, imiquimod and its derivatives, podofilox, podophyllin, interferon alpha, acyclovir, famcyclovir, valcyclovir, reticulos and cidofovir, and salts and prodrugs thereof.

Examples of anti-inflammatory agent, include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. The preferred steroidal anti-inflammatory for use in the present invention is hydrocortisone. A second class of anti-inflammatory agents which is useful in the compositions of the present invention includes the nonsteroidal anti-inflammatory agents.

Other active agents include, but are not limited to, wound healing enhancing agents, such as recombinant human platelet-derived growth factor (PDGF) and other growth factors, ketanserin, iloprost, prostaglandin $E_1$ and hyaluronic acid, scar reducing agents such as mannose-6-phosphate, analgesic agents, anesthetics, hair growth enhancing agents such as minoxadil, hair growth retarding agents such as eflornithine hydrochloride, antihypertensives, drugs to treat coronary artery diseases, anticancer agents, endocrine and metabolic medication, neurologic medications, medication for cessation of chemical additions, motion sickness, protein and peptide drugs.

In one embodiment, the substrate or carrier contains a fragrance effective for reducing stress, calming, and/or affecting sleep such as lavender and chamomile.

The amount of the active agent in the device will depend on the active agent and/or the intended use of the device. In one embodiment, the device contains a safe and effective amount of the active agent, for example, from about 0.001 percent to about 20 percent, by weight, such as from about 0.01 percent to about 5 percent, by weight, of the substrate or carrier.

In one embodiment, the substrate or carrier contains at least two active agents carrying opposite electric charges. One example of such a composition is a composition containing from about 0.5 to about 2% of salicylic acid and from about 0.01 to about 0.2% of a cationic quaternary ammonium antimicrobial agents (such as benzalkonium chloride, benzethonium chloride, methyl benzethonium chloride, and cetylpyridinium chloride), phenol, and/or chlorhexidine gluconate. The device can simultaneously deliver both active agents of opposite charges into the membrane.

General Use

The device may be used for the treatment of a barrier membrane condition (e.g., the delivery of an active agent, light, and/or electricity into skin or mucosal tissues. In one embodiment, the device is used for the treatment of skin conditions. Examples of such treatments include, but are not limited to: treatment of acne, rosacea, or other microbial infections of the skin; reduction the visible signs of skin aging (e.g., wrinkles, sagging, and age-spots); folliculitis and pseudo-folliculitis barbae; treatment of wounds and lesions (e.g., enhancing healing and scar reduction); sebum regulations (e.g., sebum reduction or oily/shining skin appearance inhibition or control); pigmentation regulation (e.g., reduction of hyperpigmentation or pigmentation of light skin); hair growth retardation (e.g., skin on the leg) or hair stimulation (e.g., scalp); and treatment of dermatitis (e.g., atopic, contact, or seborrheic dermatitis) and/or psoriasis.

In another embodiment, the device is used for the treatment of mucosal conditions (e.g., mucosa in the oral or vaginal cavities). Examples of such treatments include, but are not limited to: treatment of vaginal candidiasis and vaginosis, genital and oral herpes, cold sore, canker sore, oral hygiene, periodontal disease, and other microbial infections of the mucosa.

In another embodiment, the device induces certain desirable biological responses that facilitate the treatment of the barrier membrane conditions. These desirable biological responses may be induced by the electric current passage through the barrier membrane, and/or the electrochemically generated oxidizing materials, together with the active agents delivered by iontophoresis from the device, in treating the barrier conditions. Examples of the desirable responses of the barrier membrane may include, but are not limited to, sebum regulation (e.g., reduction of sebaceous gland activity), inhibition of anaerobotic microbial growth and establishment of a healthier membrane microflora or (e.g, reduction of $P.$ $acne$ growth and of production of irritating fatty acids), blood vasoconstriction (thus promoting local accumulation of active agents or removal of dark circle under the eye due to deoxyhemoglobins), enhanced tissue immunological activity (e.g, increased elimination of pathogenic microbes on tissue's own defense systems), improved tissue repairing (e.g., enhanced healing and reduced scarring of lesions such as acne lesions), and improved keratolytic activity (e.g., softening of keratin plugs of comedones in whiteheads and blackheads of acne, and facilitating their removal).

In one embodiment, the device is used to eliminate or reduce various types of pain or other sensory discomfort, including but not limited to, back pain, joint pain, neck pain, shoulder pain, tingling or numbness of the skin, post-surgical pain, muscle soreness, muscle cramps, menstrual cramps, joint stiffness, headache or stomach pain. When used for the pain of deeper tissues or organs other than the skin, the electrodes of the galvanic couples are larger in size and spaced farther apart in order to deliver electric stimulation deeper and to cover larger areas of the body, for example in treating back pain, knee pain, shoulder pain or neck pain.

In another aspect, the invention also features the method of converting an active agent from a less active form to a more active form via oxidation or reduction via an inert electrode (e.g., cystine to cysteine, disulfide acetyl-cysteine to acetyl-cysteine, and retinol to retinoic acid). Thus, an unstable agent can be stored in a more stable form and converted to its active form prior to administration. In a further aspect, the generation of reducing agents by the device of the present invention can be used to stabilize oxygen-labile active agents. Examples of such oxygen-labile active agents include, but are not limited to, retinoids, ascorbic acid, and benzoyl peroxide.

In one embodiment, the invention also features the method of converting an active agent from a less active form to a more active form via oxidation at a reactive anode, such as an anode made of zinc, magnesium, copper, aluminum, alloy or mixture of these metals. For example, an anode made of zinc releases zinc ions with the passage of an electric current through the electrode. The zinc ions generated by such an electrochemical reactions are then subsequently delivered by the electric repulsion of the positively charged anode into the barrier membrane. In one embodiment, such ions are deposited into the hair follicles and/or sebaceous glands to inhibit $P.$ $acnes$ growth and/or suppress skin tissue inflammation resulted from $P.$ $acnes$ over growth before the treatment. Similarly, a zinc-copper alloy anode or another zinc-beneficial metal alloy releases both zinc ions and copper ions or the other beneficial ions, respectively, into the hair follicles and sebaceous glands for acne treatment and prevention.

In one embodiment, the device of the present invention is used to treat skin conditions such as: acne (e.g., blackheads and whiteheads) and acne-related skin conditions such as rosacea and nodule-cystic; hyperpigmentation such as freckles, melasma, actinic and senile lentigines, age-spots, post-inflammatory hypermelanosis, Becker's naevus, dark circles under the eye, and facial melanosis; stretch marks; and skin aging effects on the skin (such as those caused by photodamage) including wrinkling, roughness, pigmentary alterations, sallowness, fine lines, and laxity, by delivering active agents that including pre-formulated active agents in the carrier and electrochemically generated active agents (e.g., beneficial metal ions) by the electrodes, and/or by providing electric stimulation to the skin tissues.

In one embodiment, the device provides multiple mechanisms of action to treat such conditions: namely, (a) target-delivering pre-formulated active agents into the pilosebaceous unit by iontophoresis and electro-osmosis; (b) electrochemically generating new active agents (e.g., the beneficial metal ions from a reactive anode) and targeted delivery of the freshly generated active agents to the pilosebaceous unit (e.g., beneficial ions such as zinc and copper have known to enhance skin's own immune system); and/or (c) providing electric stimulation to the pilosebaceous unit and its surrounding skin tissues to increase blood circulation, and to treat the skin by reducing inflammation, enhancing wound healing, and/or increasing skin exfoliation.

In one embodiment, the device of the present invention can be used as or incorporated into wound dressings and bandages to provide electric therapy for healing enhancement and scar prevention. In one embodiment, the wound exudation fluid and/or wound cleansing solution serves to activate a galvanic wound dressing/bandage to deliver active agents pre-incorporated in the wound dressing/bandage and/or to generate electrochemically beneficial metal ions followed with delivery of the beneficial metal ions into the wound. The device also treats the wound with therapeutic electric current which may increase blood circulation, stimulate tissue immune response, and/or suppress tissue inflammation, which may lead to accelerated healing and reduced scarring.

In one embodiment, the device of the present invention is for use as a dry wipe, towel, or full or partial facial mask (for example, having a surface area of from about 20 $cm^2$ to about 10,000 $cm^2$), which may be wetted immediately before use by applying water to the device or to the skin (e.g., by washing with tap water). In another embodiment, the device of the present invention is for use as a therapeutic patch or mask for application to a portion of or substantially all of the face (for example, having a surface area of from about 1 $cm^2$ to about 600 $cm^2$).

Booster Patch

In one particular embodiment, the device is configured as a booster patch for use with other skin treatments, for example facial masks. Accordingly, a skin treatment product is provided that comprises a facial mask, preferably a wet facial mask, and the device of the invention.

In another embodiment, the device is configured as a booster patch that may be applied directly to the skin with using a carrier.

In one embodiment, the substrate of the booster patch is not absorbent (e.g., the substrate comprises a PET film) and the printed face of the booster patch is oriented towards the skin.

In another embodiment, the substrate of the booster patch is an absorbent material such as but not limited to paper, and electrical current may flow through the substrate as well as through the facial mask and the skin. Therefore, either face of the booster patch may be oriented toward the skin. For applications where the absorbent booster patch is used with a facial mask, it is preferred that the face on which the galvanic couples lie (i.e., the face on which the first and second conductive electrodes are printed) be applied towards the mask. For applications where the absorbent booster patch is used alone with no mask, it is preferred that the unprinted face of the booster patch be placed against the skin.

In one embodiment, active ingredients may be deposited onto a dry booster patch, for example on the substrate.

Adhesion between the booster patch and facial mask or skin is important and can be achieved by several methods. Preferably, surface forces between fluid contained within the facial mask and the booster patch substrate provide adequate strength such that the booster patch will readily adhere to the wet facial mask or skin. If this is not the case, surface properties of the substrate of the booster patch, facial mask liquid, or facial mask material may be modified to facilitate adequate adhesion. In one embodiment, surface modification can be achieved by corona treatment of either the substrate of the booster patch or the facial mask material to modify surface tension in such a way that adhesion is enhanced. In another embodiment, adhesion may be enhanced by adding an adhesive or dissolving polymer to the dry booster patch or facial mask material such that the formulation becomes sticky upon wetting. In another embodiment, the facial mask may comprise liquid formulated with a sticky substance, such as sodium polyacrylate and/or acrylates/C10-30 alkylacrylate crosspolymer.

In another embodiment mechanical features may be added to the booster patch to enhance adhesion with a facial mask. Such features include but are not limited to: 1) hooks, barbs, or other protrusions on the booster patch that create a mechanical connection to the facial mask substrate similar to a Velcro® effect, 2) texturization of the surface of the booster patch to increase its surface roughness, such that there is increased surface area for attraction between the booster patch and the facial mask, and 3) introduction of relief slits into the booster patch in order to increase flexibility and conformability of fit around anatomically sharp surfaces, such as the cheek bone.

FIG. 1 shows a top view of a single galvanic couple according to the invention. The galvanic couple comprises a first conductive electrode 140 and a second conductive electrode 240 on a substrate 160. The first and second conductive electrodes are in electrical communication via a connecting bridge 350 comprising a conductive material. FIG. 2 is a top view of a device according to the invention comprising a substrate 160 comprising a plurality of discrete galvanic couples of FIG. 1.

Figure 3:
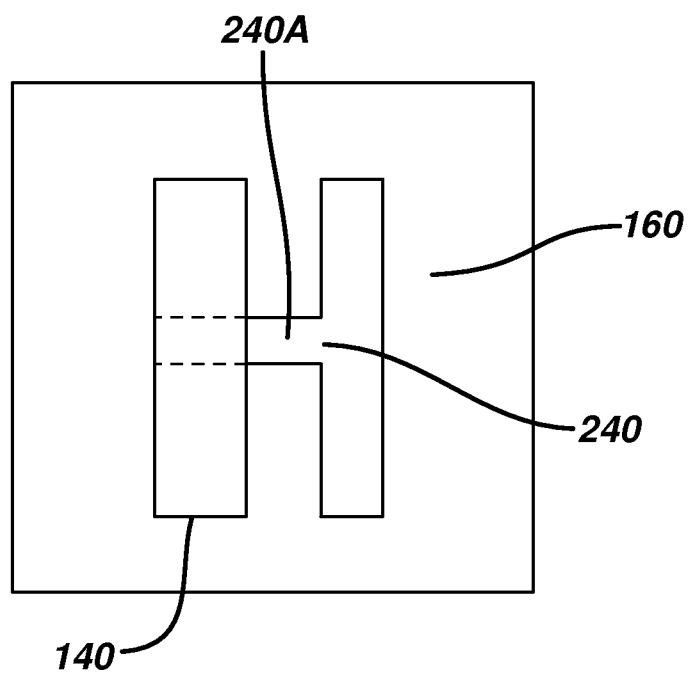
FIG. 3 is a top view of a single galvanic couple according to the invention comprising conductive electrodes 140 and 240 brought into electrical communication by a connecting bridge comprising an extension of the second conductive electrode 240A.

FIG. 3 is a top view of a single galvanic couple according to the invention comprising a first conductive electrode 140 and a second conductive electrode 240 in electrical communication via a connecting bridge 240A comprising an extension of the second conductive electrode 240. FIG. 4 is a top view a device according to the invention comprising a substrate 160 comprising a plurality of discrete galvanic couples of FIG. 3.

Figure 5:
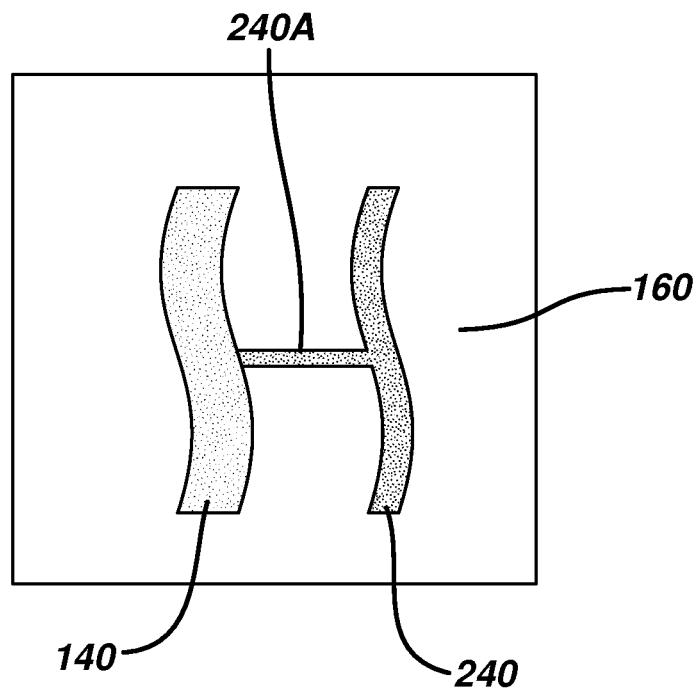
FIG. 5 is a top view of a single galvanic couple according to the invention having a wavy H-shape.

FIG. 5 is a top view of a single galvanic couple according to the invention having a wavy H-shape. The galvanic couple comprises a first conductive electrode 140 and a second conductive electrode 240 in electrical communication with each other via a connecting bridge 240A comprising an extension of the second conductive electrode.

FIG. 6 is a top view of a device according to the invention comprising a substrate 160 comprising a plurality of discrete galvanic couples as shown in FIG. 5.

FIG. 7 is a top view of a device according to the invention comprising a plurality of discrete galvanic couples as shown in FIG. 1 in a nested configuration. In this device, an array of galvanic couples is arranged on substrate 160 to increase their surface density. The first conductive electrodes 140 of the six galvanic couples are oriented to focus a single polarity towards the center of the device.

FIG. 8 is a top view of a device according to the invention for use as a booster patch. The booster patch comprises a substrate 160 of arcuate shape comprising relief slits 450 along the periphery to enhance conformability to skin surfaces. The booster patch comprises galvanic couples having a wavy H-shape, each comprising a first conductive electrode 140 in electronic communication with a second conductive electrode 240.

FIG. 9 is a top view of a skin treatment product according to the invention comprising a device 750 overlaying a facial mask 550 which is placed against the skin 650. The facial mask 550 comprises wet absorbent material, which may be loaded with a formula containing an active agent. In one embodiment the skin is facial skin. In one embodiment, the absorbent material is filter paper. In another embodiment, the absorbent material is a nonwoven material. In one embodiment, the absorbent material is in the shape of a full facemask. The booster patch 750, which comprises a plurality of discrete galvanic couples comprising first conductive electrodes 140 and second conductive electrodes 240 in electronic communication via a connecting bridge 350 on a substrate 160, is then applied to the facial mask with the conductive electrodes facing towards the skin. The wet formulation absorbed within the absorbent material provides booster patch adhesion.

EXAMPLE 1

A galvanic couple according to the invention was prepared as follows. A first conductive electrode comprising zinc and a second conductive electrode comprising silver/sliver chloride were screen printed onto a substrate comprising Mylar film. An ink formulation comprising pharmaceutically acceptable binder, plasticizer, solvent and metallic zinc was used as the material for the first conductive electrode. An ink formulation comprising pharmaceutically acceptable binder, plasticizer, solvent and silver chloride was used as the material for the second conductive electrode. Metallic silver powder was added to both inks to increase electrical conductivity of the printed traces.

The printed zinc trace was 1 mm wide by 10 mm long and was printed through a 195 mesh polyester screen. The silver/silver chloride trace was 2 mm wide by 10 mm long and was printed through a 255 mesh polyester screen. The electrodes were oriented such that the 10 mm axes were parallel to each other and separated by a 4 mm gap. The trace resistances from end to end of the zinc and silver/silver chloride electrodes were less than 100 ohms.

The electrodes were brought into electrical communication by a printed trace of conductive carbon, which was printed prior to (beneath) the zinc and silver/silver chloride traces. The conductive carbon and print dimensions were modified to provide 2000 ohms of resistance across the 4 mm gap between the electrodes. An ink formulation comprising pharmaceutically acceptable binder, plasticizer, solvent and carbon was used as the material for the conductive carbon trace.

The galvanic couple had the design shown in FIG. 1, consisting of an H-shaped pattern with zinc conductive electrode 240 and silver/silver chloride electrode 140 representing the vertical legs of the 'H' and carbon representing the connecting carbon trace 350 as the horizontal bar to form the complete galvanic couple electric source.

The galvanic couple had dimensions of about 10 mm×7 mm, and covered about 1 cm$^2$.

An array of these galvanic couples was printed using a DEK Horizon 03i commercial screen printer. The horizontal spacing between galvanic couples was set to 4 mm so that the spacing between all zinc and silver/silver chloride traces was fixed, i.e., the gap between zinc and silver/silver chloride within a galvanic couple was the same dimension as the gap between galvanic couples. Thus, an even distribution of electricity could be delivered to a treatment area. The vertical spacing between galvanic couples was 2 mm.

The current output of the galvanic couples was tested by placing a portion of nonwoven material over the printed face of the galvanic couple. The nonwoven material was wetted with a beauty formulation having a conductivity of 1300 microsiemen and current was measured with a multimeter and PC data logging station. The current range from these samples was 80-120 A per galvanic couple and lasted for 20-30 minutes.

Enhanced delivery of active compounds into the skin was confirmed by spiking the beauty formulation with a UV fluorescent molecule, salicylic acid, and placing the device against the facial skin of a volunteer for 20 minutes. Upon removal of the product, the skin was washed and UV photographs of the skin revealed an array of bright rectangles indicating iontophoretic delivery of salicylic acid into the skin.

EXAMPLE 2

In this example a plurality of discrete galvanic couple composed of zinc (anode) and silver/silver chloride (cathode) inks were screen printed onto Mylar film as described in Example 1. However, these electrodes were brought into contact and electrical communication by a protrusion of the zinc trace, also composed of zinc ink, which was connected to the silver/silver chloride trace. This protrusion, the zinc bridge, was 0.25 mm in width and 5 mm in length, and yielded a resistance of about 20 ohms across the galvanic couple. The overall design consisted of an 'H' pattern with zinc and silver/silver chloride representing the vertical legs of the 'H' and zinc representing the connecting bar as shown in FIG. 3. In essence the zinc was a "T" shape that was rotated by 90 degrees. The galvanic couple was printed in two steps as opposed to the three step galvanic couple described in Example 1. The zinc 'T' was printed prior to the silver/silver chloride trace.

An array of these galvanic couples was printed with a commercial screen printer as described in Example 1. The current output of the galvanic couples was tested as described in Example 1. The current range from these samples was 300-500 micro-A per galvanic couple and lasted for 20-30 minutes.

Enhanced delivery of active compounds into the skin was confirmed as described in Example 1 using salicylic acid. Upon removal of the product, the skin was washed and UV photographs of the skin revealed an array of bright rectangles indicating iontophoretic delivery of salicylic acid into the skin.

EXAMPLE 3

A device according to the invention was made comprising zinc and silver/silver chloride wavy electrodes. This was done to enhance the aesthetics of the galvanic couples within the array. Although the electrodes were wavy, the spacing between the zinc and silver/silver chloride traces was fixed at all points along the long axis of each galvanic couple to ensure evenly distributed electrical current between electrodes. Electrical performance and delivery of compounds into the skin were similar to that of Example 2.

EXAMPLE 4

In order to increase the density of galvanic couples in a certain area and to focus a negative pole towards a spot on the skin for enhanced electric current intensity or current density, a device was made as shown in FIG. 7. Six galvanic couples each comprising a first conductive electrode 140 and a second conductive electrode 240 were deposited on a substrate 160 using the method described in Example 1. The first and second conductive electrodes were in electrical communication via connecting bridges 350 comprising an electronically conductive material. In addition, the galvanic couples were nested to overlap such that the silver/silver chloride electrodes are focused towards the center of the array. Adjacent galvanic couples were intertwined to increase the current density at the treatment site. Nesting of galvanic couples in this manner can provide a preferential electric polarity for spot treatment applications, as well as increase the electric current density to the tissue surface under treatment. The nesting galvanic couples can be accomplished in any orientation depending on the desired effect. They can also be arranged to focus positive polarity towards one spot.

EXAMPLE 5

The following example describes a booster patch designed to adhere to a facial mask comprising a non-woven material.

Twelve two-ink galvanic couples were screen printed onto 2 mil Mylar film, which was cut to have the shape shown in FIG. 8. Four mechanical stress relief grooves were implemented in the periphery of the booster patch to enhance flexibility.

Fifteen volunteers used the booster patch with a facial mask as follows. First, the users applied the wet nonwoven facial mask to their face. Each user then applied a booster patch to the facial mask with the printed side (i.e., comprising the galvanic couples) facing towards the facial mask. The booster patch readily adhered to the wet facial mask by forces associated with surface tension alone. After 20 minutes of booster patch application, the mask and booster patch were removed.

Wear-ability and booster patch adhesion was assessed by the volunteers. The booster patch remained against the wet mask without peeling off for the full 20 minute treatment for 10 volunteers. Two volunteers reported slight peeling of the patch after 15 minutes and three subjects reported peeling prior to 15 minutes of treatment.

Enhanced delivery of active compounds into the skin was confirmed by spiking the formulation in the facial mask with salicylic acid, and placing the booster patch against the facial mask as described above for 7 volunteers. Upon removal of the product, the skin was washed with soap and water. Ultraviolet photography of the skin revealed an array of bright areas corresponding to zinc electrodes, indicating iontophoretic delivery of salicylic acid into the skin.

EXAMPLE 6

Print quality for zinc conductive ink was compared for two nonwoven substrates, one composed of pure apertured rayon and one composed of a 50/50 blend of polyethylene/pulp. Printing was done under the same printing conditions for both substrates. The printed pattern consisted of an array of 2 mm by 10 mm rectangles. For the case of the rayon substrate, conductivities of the printed traces were less than 100 ohms measured between long ends of the rectangular trace. Microscopic images showed that the fibers of the nonwoven sample were evenly coated with the ink, indicating similar surface energy. Traces printed on the polyethylene/pulp nonwoven displayed sporadic resistance values many of which were not conductive at all. Microscopic images indicated that the fibers of the nonwoven were not coated with ink. However, the ink was deposited as beads into the nonwoven matrix. This resulted in discontinuities along the printed trace which translated into high resistance values.

EXAMPLE 7

Galvanic couples made from the zinc, silver/silver chloride, and carbon inks described in Example 1 were printed onto an apertured rayon nonwoven. Microscopy revealed that the inks readily coated the rayon fibers of the nonwoven indicating wettability of the ink-rayon system. Silver/silver chloride and zinc electrode resistances were less than 100 ohms. Carbon resistance was 1000 ohms. Electrical output was measured by adding a conductive beauty solution having a conductivity of 1300 microsiemen to the printed nonwoven. Electrical current per galvanic couple was generated in the 100-150 micro-Amps range.

The resulting product was tested on human skin to assess iontophoretic delivery of a charged UV-fluorescent compound, salicylic acid, to the skin. Volunteers wet the nonwoven with a beauty gel having a conductivity of 1300 microsiemen spiked with salicylic acid and placed the unprinted side of the nonwoven against the cheek skin for 20 minutes. The product was then removed, and the skin was washed with mild soap. An ultraviolet photograph of the skin revealed an array of bright areas corresponding to zinc electrodes, indicating iontophoretic delivery of salicylic acid into the skin.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A device for treatment of skin comprising a substrate comprising a plurality of evenly spaced discrete galvanic couples, each galvanic couple comprising a first conductive electrode that is an anode in electronic communication with a second conductive electrode that is a cathode, wherein said first and second conductive electrodes each comprise an ink.

2. The device of claim 1, wherein each galvanic couple has a size of about 0.01 $cm^2$ to about 10 $cm^2$.

3. The device of claim 1, wherein each galvanic couple has a size of about 10 $cm^2$ to about 400 $cm^2$.

4. The device of claim 1, wherein said first and second conductive electrodes are in electronic communication through a connecting bridge comprising at least one conductive material.

5. The device of claim 1, wherein said first and second conductive electrodes are in electronic communication through a connecting bridge comprising an extension of said first or second conductive electrode.

6. The device of claim 1, wherein each galvanic couple has a shape selected from the group consisting of substantially H-shaped, substantially U-shaped and substantially N-shaped.

7. The device of claim 1, wherein said galvanic couples are nested on said substrate.

8. The device of claim 1, wherein said substrate comprises a material selected from the group consisting of paper, plastic, woven materials and non-woven materials.

9. The device of claim 1 further comprising a carrier suitable for contacting skin and in ionic communication with said first and second conductive electrodes.

10. The device of claim 9 further comprising an active agent in said carrier.

11. The device of claim 1, wherein the difference in standard potentials of the first and second conductive electrodes is at least about 0.2 V.

12. The device of claim 1 further comprising an active agent in said substrate.

13. The device of claim 1, wherein said first conductive electrode comprises zinc, magnesium, iron, aluminum, alloys thereof, or mixtures thereof, and said second conductive electrode comprises copper, iron, gold, silver, platinum, carbon, alloys thereof, oxides thereof, halides thereof, or mixtures thereof.

14. A method of treating skin, comprising applying to said skin a device comprising a substrate comprising a plurality of evenly spaced discrete galvanic couples, each galvanic couple comprising a first conductive electrode that is an anode in electronic communication with a second conductive electrode that is a cathode, wherein said first and second conductive electrodes each comprise an ink.

15. The method of claim 14, wherein said skin is in need of treatment for a condition selected from the group consisting of pigmentation, skin tone, skin puffiness, dark circles around the eye, skin wrinkles, skin fine lines, hair growth, skin texture, skin firmness, skin elasticity, skin vasculature, skin circulation, cellulite, sebum regulation, skin shine, acne, rosacea, impetigo, folliculitis, furunculosis, ecthyma, eczema, psoriasis, atopic dermatitis, herpes, epidermolysis bullosa, icthyosis, and infected traumatic lesions.

16. The method of claim 14, wherein each galvanic couple has a size of about 0.01 cm$^2$ to about 10 cm$^2$.

17. The method of claim 14, wherein each galvanic couple has a size of about 10 cm$^2$ to about 400 cm$^2$.

18. The method of claim 14, wherein said first and second conductive electrodes are in electronic communication through a connecting bridge comprising at least one conductive material.

19. The method of claim 14, wherein said first and second conductive electrodes are in electronic communication through a connecting bridge comprising an extension of said first or second conductive electrode.

20. The method of claim 14, wherein each galvanic couple has a shape selected from the group consisting of substantially H-shaped, substantially U-shaped and substantially N-shaped.

21. The method of claim 14, wherein said galvanic couples are nested on said substrate.

22. The method of claim 14, wherein said substrate comprises a material selected from the group consisting of paper, plastic, woven materials and non-woven materials.

23. The method of claim 14 further comprising a carrier suitable for contacting skin and in ionic communication with said first and second conductive electrodes.

24. The method of claim 23 further comprising an active agent in said carrier.

25. The method of claim 14, wherein the difference in standard potentials of the first and second conductive electrodes is at least about 0.2 V.

26. The method of claim 14 further comprising an active agent in said substrate.

27. The method of claim 14, wherein said first conductive electrode comprises zinc, magnesium, iron, aluminum, alloys thereof, or mixtures thereof, and said second conductive electrode comprises copper, iron, gold, silver, platinum, carbon, alloys thereof, oxides thereof, halides thereof, or mixtures thereof.

28. A skin treatment product comprising a facial mask and a device comprising a substrate comprising a plurality of evenly spaced discrete galvanic couples, each galvanic couple comprising a first conductive electrode that is an anode in electronic communication with a second conductive electrode that is a cathode, wherein said first and second conductive electrodes each comprise an ink said device of a shape and size suitable for overlaying or underlying said facial mask during application of said facial mask and said device to skin.

* * * * *